(12) United States Patent
Shaknovich

(10) Patent No.: US 6,572,652 B2
(45) Date of Patent: Jun. 3, 2003

(54) METHOD AND DEVICES FOR DECREASING ELEVATED PULMONARY VENOUS PRESSURE

(75) Inventor: Alexander Shaknovich, New York, NY (US)

(73) Assignee: VenPro Corporation, Irvine, CA (US)

( * ) Notice: Subject to any disclaimer, the term of this patent is extended or adjusted under 35 U.S.C. 154(b) by 11 days.

(21) Appl. No.: 09/813,182

(22) Filed: Mar. 20, 2001

(65) Prior Publication Data
US 2002/0026233 A1 Feb. 28, 2002

Related U.S. Application Data

(60) Provisional application No. 60/228,574, filed on Aug. 29, 2000.

(51) Int. Cl.[7] .................. A61F 2/06; A61F 2/24
(52) U.S. Cl. ............ 623/2.11; 623/1.24; 623/904
(58) Field of Search ............... 623/1.24, 1.26, 623/1.31, 2.11, 2.1–2.42, 902–904; 606/153, 157, 158

(56) References Cited

U.S. PATENT DOCUMENTS 4,995,857 A * 2/1991 Arnold ................. 623/904
6,092,526 A * 7/2000 LaFontaine et al. ....... 623/1.24
6,110,201 A * 8/2000 Quijano et al. ........... 623/1.24
6,254,564 B1 * 7/2001 Wilk et al. ............... 623/1.24
6,299,637 B1 * 10/2001 Shaolian et al. ......... 623/1.24
6,302,917 B1 * 10/2001 Dua et al. ................ 623/23.7

FOREIGN PATENT DOCUMENTS

| WO | WO 9014804 | 12/1990 |
|----|------------|---------|
| WO | WO 9857599 | 12/1998 |
| WO | WO 0048531 | 8/2000 |

* cited by examiner

Primary Examiner—Danton D. DeMille
Assistant Examiner—Quang D. Thanh
(74) Attorney, Agent, or Firm—Knobbe, Martens, Olson & Bear, LLP

(57) ABSTRACT

The present invention relates to the implantation of one or more prosthetic valve(s) in the pulmonary vein(s) of a subject for decreasing or preventing an increase in pulmonary venous pressure. The present invention accordingly provides for novel treatment strategies for the treatment of medical disorders associated with elevated pulmonary venous pressure, including congestive heart failure, as well as for prosthetic pulmonary vein valves and their delivery systems. Expandable as well as fixed-dimension non-expandable pulmonary vein prosthetic valves for implantation by a variety of surgical and percutaneous procedures are also described.

13 Claims, 19 Drawing Sheets

METHOD AND DEVICES FOR DECREASING ELEVATED PULMONARY VENOUS PRESSURE

SPECIFICATION

This application claims priority to U.S. Provisional Application No. 60/228,574, filed Aug. 29, 2000.

INTRODUCTION

The present invention relates to the implantation of one or more prosthetic valve(s) in the pulmonary vein(s) of a subject as a means of decreasing or preventing an increase in pulmonary venous pressure. The present invention accordingly provides novel strategies for the treatment of medical disorders associated with elevated pulmonary venous pressure, including congestive heart failure, as well as for prosthetic pulmonary vein valves and their delivery systems. Expandable as well as fixed-dimension non-expandable pulmonary vein prosthetic valves for implantation by a variety of surgical and percutaneous procedures are also described.

BACKGROUND OF THE INVENTION

Physiologic Venous Valves

Certain larger veins in the lower extremities of human beings normally have valves that, under conditions of normal function, permit movement of blood largely only toward the heart. In effect, properly functioning venous valves in the lower extremities protect, or partition, the veins of the lower extremities from the relatively high hydrostatic pressure of the column of venous blood between the right atrium and the lower extremities due to the effect of gravity during upright posture. Thus, normally, when upright posture is assumed, venous blood pressure in the foot is generally less than the sum of relatively low pressure in the right atrium and relatively high hydrostatic pressure of the column of venous blood between the right atrium and the foot due to the effect of gravity. When these venous valves in the lower extremities are incompetent, venous blood pressure in the foot becomes predominantly equal to the sum of the relatively low pressure in the right atrium and relatively high hydrostatic pressure of the column of venous blood between the right atrium and the foot, often resulting in pathologic dilatation of the veins in the lower extremities and/or edema.

Prosthetic Valves

A prosthetic valve is an endoprosthesis typically formed of biological, synthetic or composite material, the final deployed diameter of which is suitable for implantation in the intended location in the heart or vascular conduits, such as arteries or veins. A prosthetic valve, when implanted and operating as intended, predictably directs the flow of blood through it. For example, a prosthetic aortic valve allows expulsion of blood from the left ventricle into the aorta during systole, and prevents reflux of blood into the left ventricle from the aorta during diastole. When used for replacement or repair of diseased native cardiac or vascular valves, prosthetic valves may relieve inappropriate obstruction to normally directed blood flow by narrowed or stenotic valves, or may restore appropriate hindrance to abnormally directed blood flow caused by leaking or regurgitant valves. Prosthetic valves are usually implanted by means of open surgical procedures, under general anesthesia and often with ventilatory and circulatory support, in which a surgeon exposes a diseased target valve to be replaced, resects and removes it, and implants an appropriate prosthetic valve in its place. Various types and designs of prosthetic valves for diverse clinical applications related to damage to and/or inappropriate function of the native cardiac valves have been described since the original report by Hufnagel et al., 1954, Surgery 35:573. A number of United States Patents have been issued relating to methods for percutaneous delivery of prosthetic valves and associated delivery methods, including, but not limited to, U.S. Pat. No. 5,332,402 by Teitelbaum, U.S. Pat. No. 5,397,351 by Pavenik et al., U.S. Pat. No. 5,607,465 by Camilli, U.S. Pat. No. 5,855,601 by Bessler et al., U.S. Pat. No. 5,163,953 by Vince, and U.S. Pat. No. 5,411,552 by Andersen et al.

Consequences of Elevated Pulmonary Venous Pressure

In human beings there usually are four pulmonary veins, two left and two right, draining into the left atrium. Pulmonary veins are not known to have directional valves in humans or other mammals. Under normal conditions, the pressure at a site in the pulmonary veins is, with a phase shift dependent on the distance from the left atrium, essentially the same as the pressure in the left atrium. Thus, protection, or partitioning, of the pulmonary veins from the high systolic pressure of the contracting left ventricle is the same as the protection of the left atrium, and is dependent upon proper function of the mitral valve.

The mitral valve may become regurgitant due to damage or malfunction of the valve leaflets, the annulus, the chordae tendinae, or the papillary muscles, or because of dilatation of the left ventricle. When mitral valve function is compromised, partitioning of the left ventricle during systole from the left atrium, and therefore from the pulmonary veins, becomes impaired. As a result, relatively high left ventricular systolic pressure is transmitted, with a phase shift, into the pulmonary veins, often producing marked elevation of the mean pulmonary venous pressure, which can lead to pulmonary edema and congestive heart failure ("CHF").

CHF is a major cause of cardiovascular morbidity and mortality, affecting tens of millions of patients worldwide. Current treatment of chronic CHF often relies on life-long medical therapy. CHF is a complex syndrome of various etiologies associated, in some patients, with abnormally high pulmonary venous pressures at rest and/or in conjunction with physical, emotional or metabolic stress. Whenever possible, CHF largely due to mitral regurgitation is treated with surgical replacement of the mitral valve with a prosthetic valve. In a substantial number of patients, surgical valve replacement is not possible, or is associated with an unacceptably high risk of morbidity and/or mortality.

In certain patients the left ventricle may become non-compliant, or stiff, due to a variety of conditions such as, but not limited to, ischemic heart disease, hypertension, aortic stenosis, diabetes mellitus or aging. In other patients, the mitral valve becomes narrowed or stenotic and fails to open properly during diastole. Transfer of blood into a non-compliant left ventricle or across a stenotic mitral valve during diastole can only be effected when the left atrial, and therefore pulmonary venous, diastolic pressure is markedly elevated. In such patients, signs and symptoms of CHF may develop due to markedly elevated diastolic and mean pressure in the left atrium which is transmitted to the pulmonary veins. To date, CHF due to diastolic left ventricular dysfunction can only be treated with medications, with variable efficacy. Mitral stenosis can be relieved in most patients by surgical or balloon commissurotomy or with mitral valve replacement.

SUMMARY OF THE INVENTION

The present invention generally relates to a novel strategy for treatment of disorders associated with elevated pulmonary venous pressure involving implanting, in a subject, one or more endoprosthesis ("valve"), preferably in or at the ostia of a pulmonary vein(s).

It is an object of this invention to provide for methods and devices which lower mean pulmonary venous pressure, and thereby treat conditions such as congestive heart failure ("CHF"), by creating an effective unidirectional partitioning between the left atrium and one or more of the four pulmonary veins. The present invention provides for expandable as well as fixed-dimension prosthetic valves for implantation in or at the pulmonary veins of appropriately selected patients with existing, impending or probable CHF.

The prosthetic valves of the invention, in their properly implanted condition, configuration and orientation, are capable of permitting ingress of blood from the pulmonary vein(s) into the left atrium during that portion of the cardiac cycle when the pressure in the pulmonary vein(s) slightly exceeds the pressure in the left atrium, and are capable of preventing egress of blood from the left atrium into the pulmonary vein(s) during that portion of the cardiac cycle when the pressure in the left atrium slightly exceeds the pressure in the pulmonary vein(s).

In further embodiments, the present invention relates to particular species of expandable prosthetic pulmonary valves, to said valves comprised in delivery systems, and to strategies for percutaneous or surgical delivery, placement and implantation of said valves. Specific examples include the diaphragm, trapdoor, stocking and windsock valves illustrated in FIGS. 1–4, respectively.

In preferred embodiments of the invention, pulmonary vein prosthetic valves, when implanted in one or more pulmonary vein(s), are intended to relieve or eliminate CHF due to mitral valve regurgitation and/or left ventricular non-compliance. In patients with CHF with abnormally high mean pulmonary venous pressure due to defective systolic partitioning between the left ventricle and the pulmonary veins largely or partially secondary to mitral regurgitation, who are deemed unsuitable for mitral valve replacement, implantation of prosthetic pulmonary vein valves may be used to lower mean pulmonary venous pressure by restoring effective systolic partitioning between relatively high left ventricular and left atrial systolic pressure, and pulmonary veins. In patients with CHF largely or partially due to left ventricular diastolic dysfunction or mitral stenosis, with abnormally high mean pulmonary venous pressure due to natural lack of diastolic partitioning between the left atrium and pulmonary veins, implantation of the prosthetic pulmonary vein valves may be used to lower mean pulmonary venous pressure by creating effective diastolic partitioning between relatively high left atrial diastolic pressure and the pulmonary vein(s).

DETAILED DESCRIPTION OF THE INVENTION

Prosthetic Pulmonary Valves

Figure 1A:
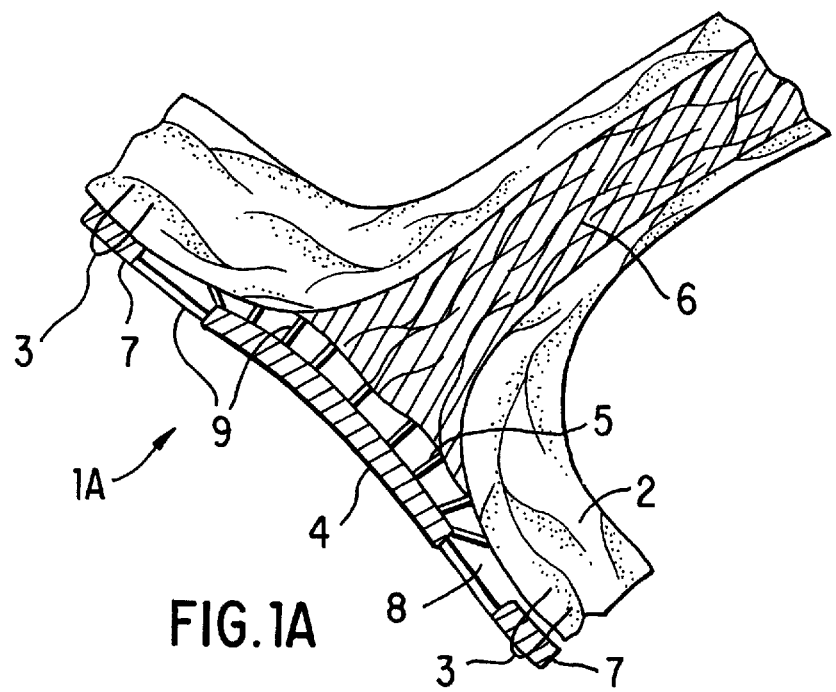
FIGS. 1A–D depict various views and embodiments of the diaphragm-type prosthetic pulmonary vein valve. (A) and (B) show, respectively, a transverse sectional view and a top view of a surgically implanted diaphragm valve, showing the valve positioned over an ostium of a pulmonary vein in the left atrium. (C) and (D) show, respectively, transverse sectional views of a diaphragm valve in open and closed positions, where the valve is held in place over a pulmonary vein ostium by an anchoring stent located in the pulmonary vein. The diaphragm valve has fenestrations, such that when the pressure in the pulmonary vein exceeds that of the left atrium, blood may flow through the fenestrations (C), but, when the pressure in the left atrium becomes greater than that in the vein (D), the occluder portion of the valve creates an obstruction to blood flow and/or the transmission of pressure into the pulmonary vein (D).
Figure 1B:
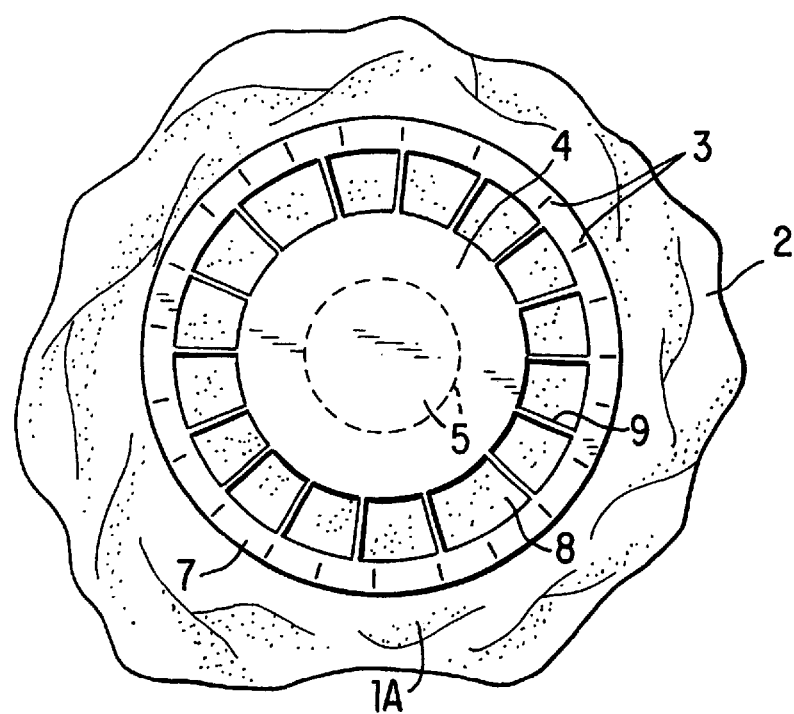

The present invention provides for prosthetic pulmonary valves, systems and methods for their delivery, and methods of using such valves for treating subjects exhibiting or at risk for developing elevated pulmonary venous pressures.

The term "prosthetic", as used herein, refers to the fact that the valves of the invention are implanted into subjects, and does not suggest that the valves replace any naturally occurring valve, as pulmonary vein valves are not known to occur in mammals.

An expandable pulmonary vein prosthetic valve for percutaneous delivery, placement and implantation or for implantation during surgical procedures desirably exhibits a smaller relative circumference and area in its unexpanded configuration to facilitate delivery and placement. That portion of a valve which is retained within the pulmonary vein preferably conforms to the dimensions of the vein, particularly the diameter of the vein in transverse section. Location, number, and diameter of the proximal pulmonary veins can be reliably ascertained non-invasively, at present utilizing magnetic resonance imaging or trans-esophageal echocardiography. The average diameter of the most distal segment of a pulmonary vein draining directly into the left atrium in humans was found by Horsfield and Gordon (Lung 81:159: 211–218) to be 13.9 mm (range, 12.5–17.0 mm), which may be increased in certain pathological conditions. The average length of the same segment distal to the last bifurcation point was 36.7 mm (range, 28–52.3 mm). Accordingly, that portion of the prosthetic valve (which may, in specific embodiments, constitute the entire valve) which resides in the pulmonary vein preferably has a diameter of between 10 and 20 mm (inclusive). A portion of a valve which, during at least part of its operation, is located in the left atrium may have one or more dimensions which exceed the foregoing values. Indeed, in certain non-limiting embodiments, the prosthetic valve may be located entirely in the left atrium. For example, a diaphragm- or trapdoor-type valve (as shown in FIGS. 1 and 2) preferably has an occluder portion (see infra) having a diameter which exceeds the maximum diameter of the ostium; in non-limiting embodiments of the invention, the occluder portion has a diameter measuring between 10 and 25 mm. In prosthetic valves which comprise a portion that is retained within the pulmonary vein, such as the stocking-type or windsock-type of valves shown in FIGS. 3 and 4, that portion retained in the vein preferably has a length which does not exceed the length of vein extending from the left atrium to the first-encountered venous bifurcation; in non-limiting embodiments, this length may be between 3 and 30 mm.

An expandable pulmonary vein prosthetic valve may be self-expandable when released from its unexpanded configuration, or may be non-self-expandable and only expandable by means ancillary to the prosthetic valve itself. The means for expansion for non-self-expanding pulmonary vein prosthetic valves may be intrinsic or extrinsic to the pulmonary vein prosthetic valve delivery system.

A fixed-dimension pulmonary vein prosthetic valve for implantation during open-heart surgical procedures typically has a single insertion and implantation circumference and area. Such fixed-dimension prosthetic valves may have an insertion system for valve positioning and anchoring during open-heart pulmonary vein prosthetic valve implantation.

In one non-limiting embodiment, the present invention provides for a diaphragm-type prosthetic pulmonary vein valve device. FIG. 1A depicts a specific embodiment of such a valve (1), which is surgically anchored to the wall of the left atrium (2) by sutures or staples (3). The valve comprises an occluder portion (4), which is positioned over the ostium (5) of a pulmonary vein (6). The valve comprises an anchoring portion (7) encircling the occluder portion, which serves as a means for attachment of the valve device to the atrial wall, and which receives the sutures or staples (3). The area between the anchoring portion (7) and the occluder portion (4) contains one or more fenestration (8) with a bridging arm(s)(9) between. The bridging arm(s)(9) flexibly join the occluder portion (4) to the anchoring portion (7), and permit movement of the occluder portion outside of the plane defined by the anchoring portion, for example, but not limited to, movement perpendicular to this plane such that the occluder portion is displaced to a planar position approximately parallel to the plane of the anchoring portion. This particular embodiment of valve may be inserted by open heart surgery.

FIG. 1A is representative of a view referred to herein as a "transverse sectional view". That term, as used. herein, refers to a representation of the pulmonary vein as it enters the left atrium, as if the vein, as well as any structures in it, had been bisected parallel to its longitudinal axis and the viewer is looking at the structures remaining after one section has been removed. Accordingly, the back wall of the vein is visible, and the side walls of the vein and atrium are seen in cross-section. In FIG. 1A, the valve device is seen in cross section such that the occluder portion (4) is cut along its maximum diameter and the bridging arms (9) extending back to the atrial wall are visible.

Figure 1C:
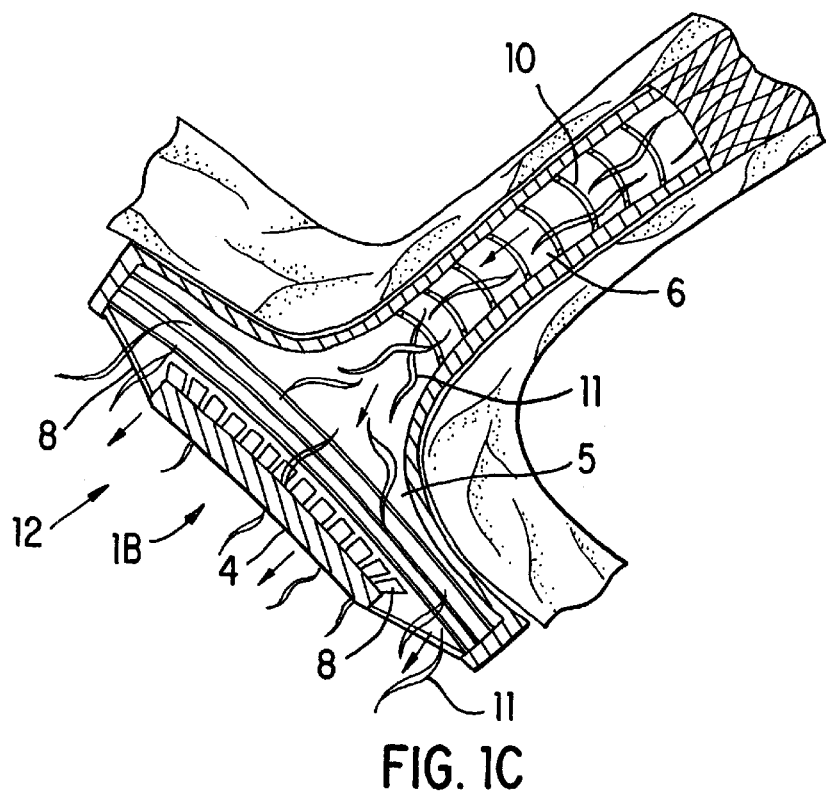
Figure 1D:
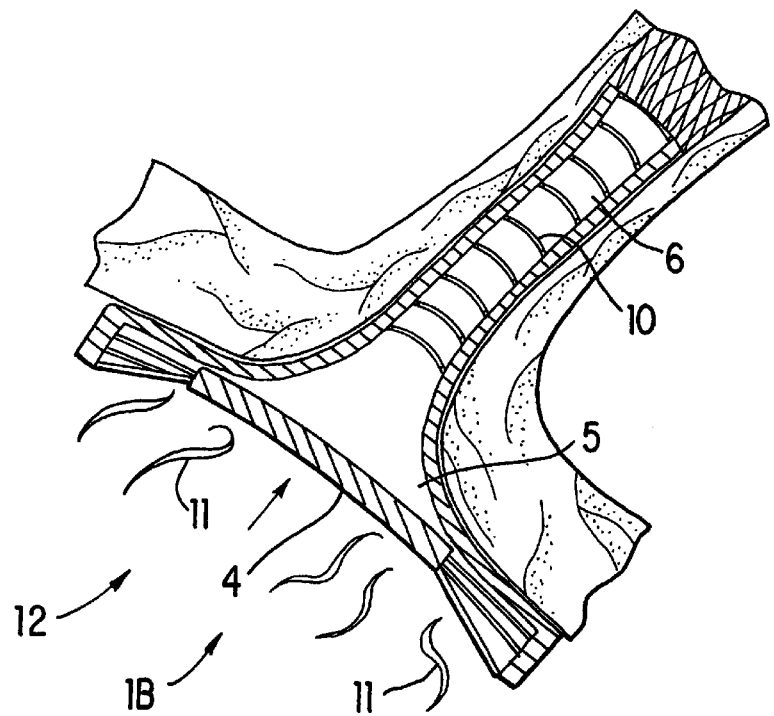

FIGS. 1C–D are transverse sectional views of another species of diaphragm-type prosthetic pulmonary valve device, wherein the valve device (1B) is maintained in position via an anchoring stent (10). FIG. 1C illustrates the situation where the pressure (arrow) of blood (shown by wavy lines, 11) in the pulmonary vein (6) is greater than the pressure in the left atrium (12) so that the occluder portion (4) is pushed away from the pulmonary vein ostium (5) into the open position, and blood flows out of the pulmonary vein through the fenestrations (8). FIG. 1D illustrates the situation where the pressure (arrow) of blood (11) in the left atrium (12) exceeds the pressure in the pulmonary vein (6), so the occluder portion (4) is pushed toward the pulmonary vein ostium (5) into the closed position, producing a partial or complete obstruction to retrograde blood flow and/or transmission of pressure. In the embodiments depicted by both FIGS. 1C and 1D, the flexibility of the bridging arms facilitates the displacement of the occluder portion of the device into the open or closed position.

Figure 2A:
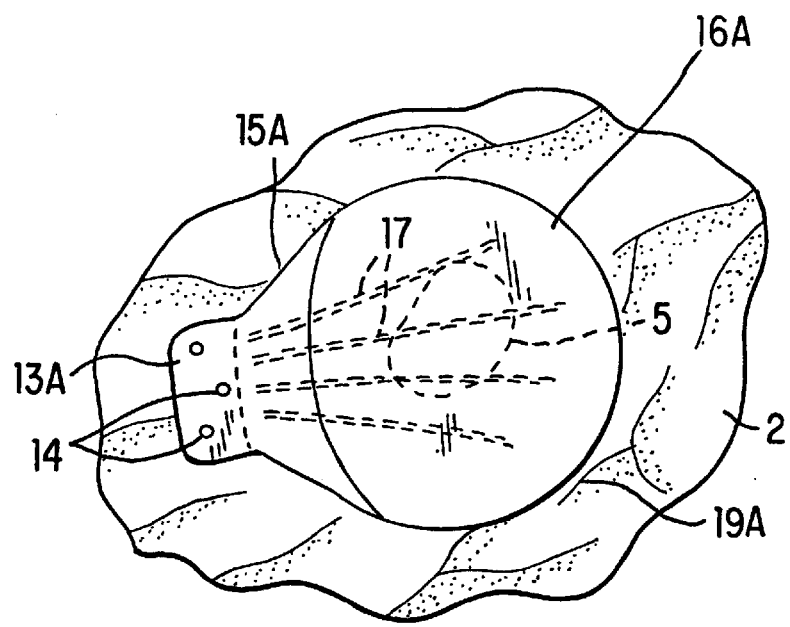
FIGS. 2A–D depict various views and embodiments of the trapdoor-type prosthetic pulmonary vein valve. (A) and (B) show top views of surgically implanted trapdoor valves positioned over an ostium of a pulmonary vein in the left atrium. The valve shown in (A) is attached to the atrium by a hinge region surgically secured to the atrial wall; the "trapdoor" covers the ostium of a pulmonary vein and, in closed position, rests against the atrial wall. The valve shown in (B) is similar, but the point of attachment encircles the pulmonary vein ostium, such that when the "trapdoor" is in closed position, it rests, in part, against the outer circumference of the valve device. (C) and (D) show transverse sectional views of a valve of the species shown in (B), in closed and open positions, respectively.
Figure 2B:
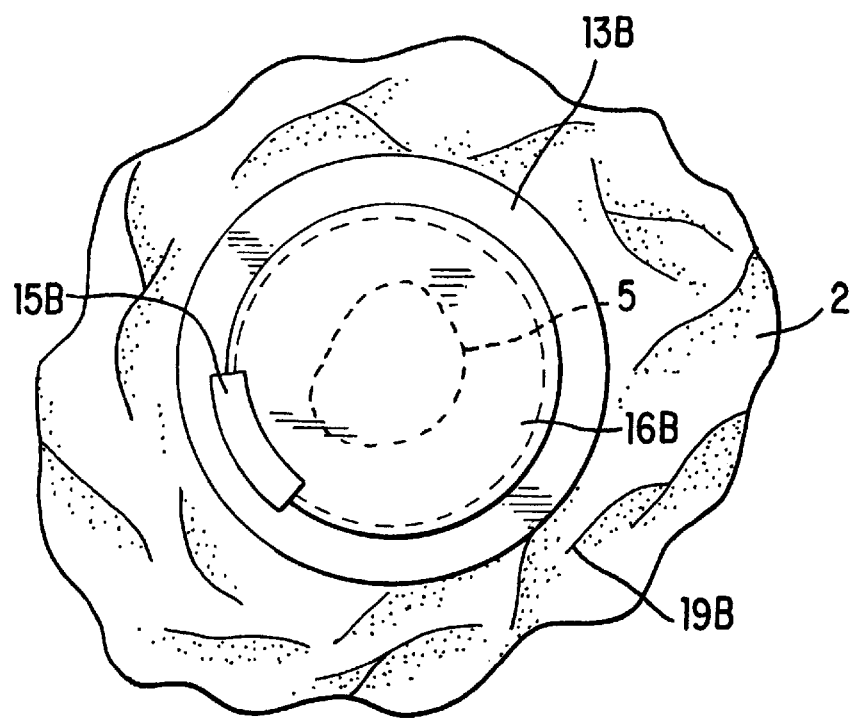

FIGS. 2A and 2B depict specific non-limiting embodiments of trapdoor-type prosthetic pulmonary vein valve devices (19A and 19B, respectively). Both are top views, showing the valve device positioned over the pulmonary vein ostium (5) and in apposition to the left atrial wall. The embodiment illustrated in FIG. 2A includes an anchoring portion (13A) optionally containing one or more eyelets (14) for sutures, a backstop portion (15A) and a flap-like occluder portion (16A). The junction between the occluder portion and the backstop portion functions as a hinge, but the backstop portion deters and preferably prevents the occluder portion from opening to so wide an angle that an increase in atrial pressure would retain the valve in the open position, with the occluder portion pressed toward the backstop. It may be preferable to fabricate the backstop portion from a rigid material, or to configure the backstop portion as a ridge-like structure, with the ridge extending approximately parallel to the line of flexion between the occluder portion and the remainder of the device. Optional spines (17) fabricated from a more rigid material may be used to stabilize the position of the occluder portion. When the occluder is in closed position, it is pressed toward the atrial wall over the ostium, creating an obstruction to blood flow/pressure transmission, and may contact the atrial wall directly.

In the related embodiment depicted in FIG. 2B, the anchoring portion (13B) substantially or completely encircles the pulmonary vein ostium (5), and is attached to occluder portion (16B) via a backstop portion (15B). When the occluder is in closed position, it is moved toward and may contact the anchoring portion. The embodiments illustrated in FIGS. 2A and 2B may be surgically attached to the atrial wall by suture(s), staple(s), or glue, or may be held in place by a surgically or percutaneously introduced anchoring stent.

Figure 2C:
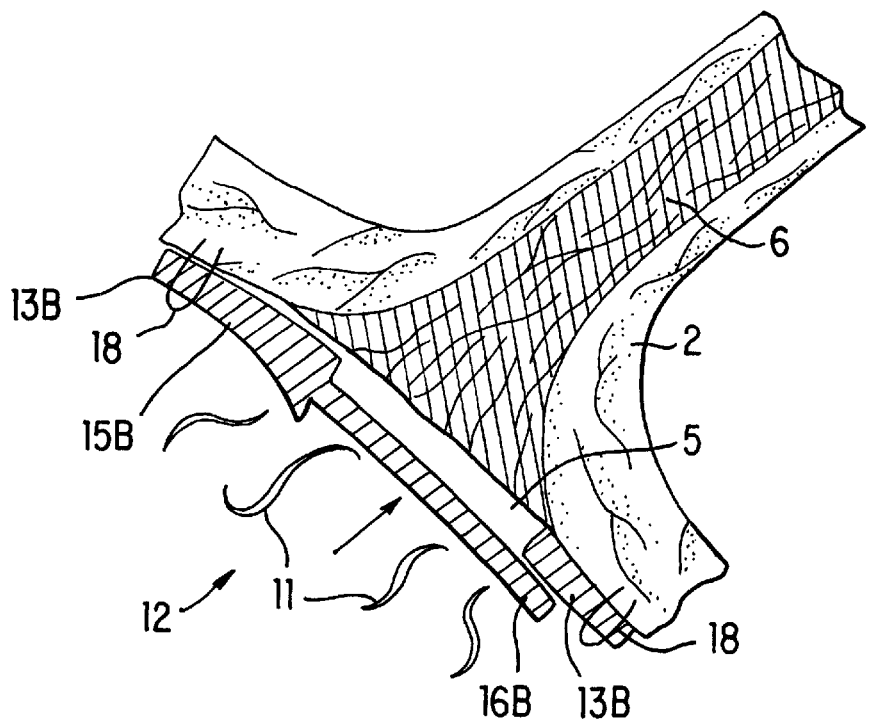
Figure 2D:
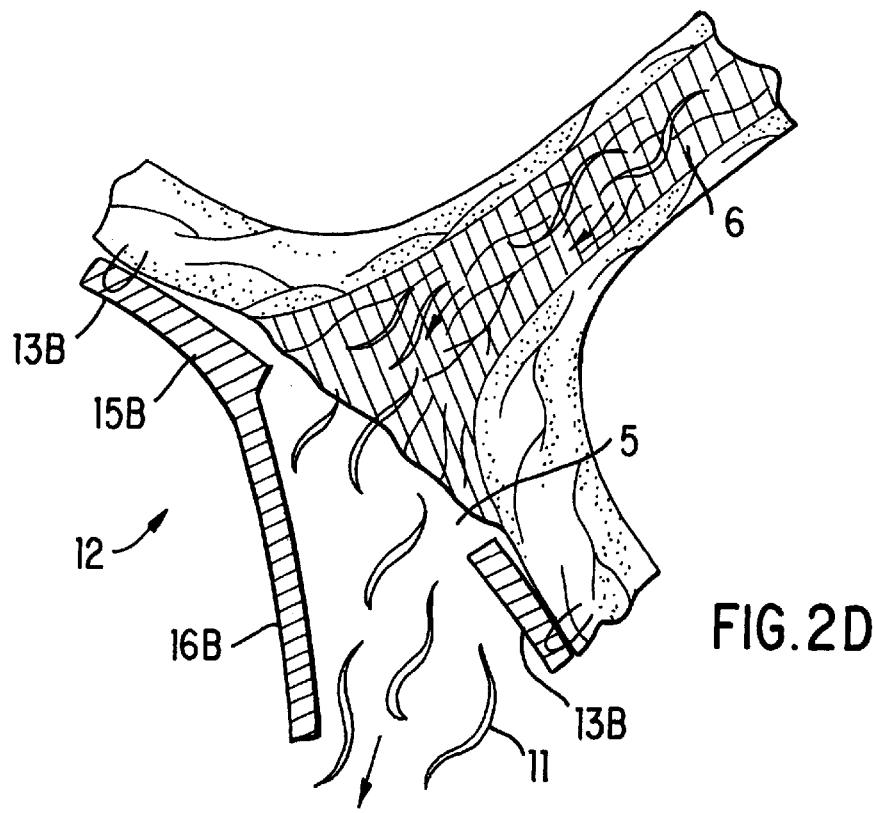

FIGS. 2C and 2D are transverse sectional views which depict the operation of a trapdoor-type pulmonary vein prosthetic valve device of the species illustrated in FIG. 2B. In both FIGS. 2C and 2D, that portion of the valve device extending from the plane of section into the page is not shown, to increase clarity of presentation. FIG. 2C shows that when the pressure in the left atrium(arrow) of blood (11) in the left atrium (12) is greater than the pressure in the pulmonary vein (6), the occluder portion (16B) is pressed toward the anchoring portion (13B) into the closed position, producing an obstruction to blood flow/pressure transmission through the ostium of the pulmonary vein. Note that the anchoring portion, in this embodiment, is attached to the atrial wall (2) with sutures (18).

FIG. 2D shows that when the pressure (arrows) of blood (11) in the pulmonary vein (6) exceeds the pressure in the left atrium (12), the occluder portion (16B) is pressed toward the left atrium into the open position, allowing blood to flow into the atrium. Note that the backstop portion (15B) deters or prevents the occluder portion from opening so widely as to be pressed toward the backstop portion, thereby preventing the occluder portion from being lodged in the open position throughout the cardiac cycle.

Figure 3A:
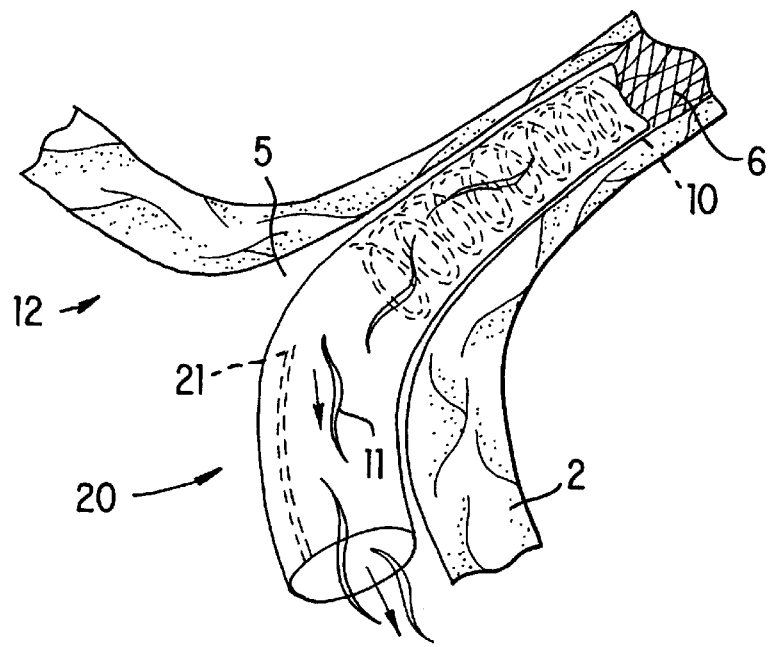
FIGS. 3A–B depict cut away views of a stocking-type prosthetic pulmonary vein valve, held in place in a pulmonary vein and extending into the left atrium, in open and closed positions, respectively.
Figure 3B:
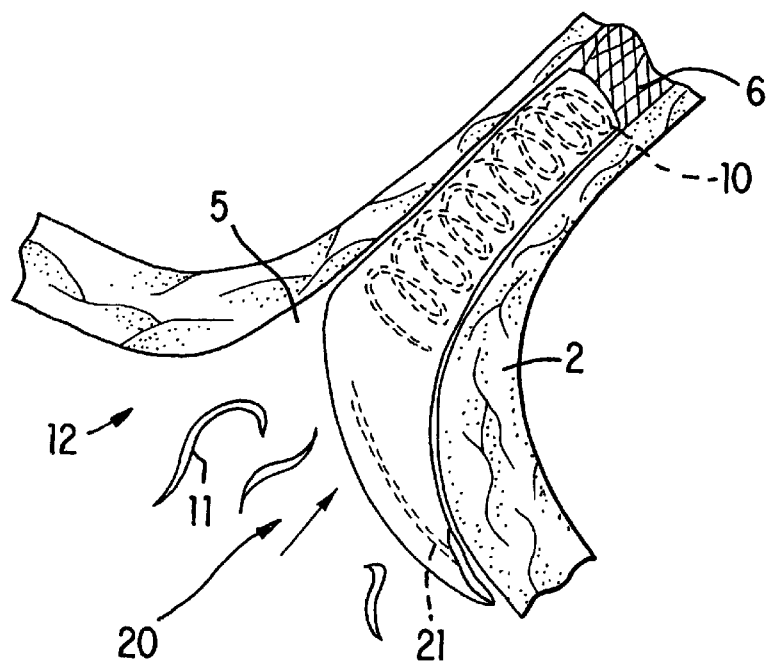

FIGS. 3A and 3B are cut away views of non-limiting examples of a stocking-type pulmonary vein valve prosthetic device (20). A "cut away view", as that term is used herein, differs from the "transverse sectional view" in that the valve device is not sectioned, but is seen intact within a sectioned pulmonary vein and atrium. Structures within the valve device (e.g., the anchoring stent) are shown by broken lines. As shown in FIGS. 3A and 3B, the device has an essentially curved tubular (stocking-like) shape, and is fabricated from flexible material. The device optionally contains a rigid spine (21) along its greater curvature which contributes stability to the device in either the open or closed positions. The embodiments shown are retained in place by an anchoring stent (10) located in the pulmonary vein (6). FIG. 3A shows that when the pressure (arrow) of blood (11) in the pulmonary vein exceeds the pressure in the left atrium (12), the flexible tube opens and allows the flow of blood into the left atrium. FIG. 3B shows that when the pressure (arrow) in the left atrium (12) exceeds that of the pressure in the pulmonary vein (6), the atrial portion of the device is pressed partially or completely closed, optionally with the functional aid of the rigid spine (21), therefore obstructing the backflow of blood and/or transmission of pressure into the pulmonary vein. Such devices may be surgically or percutaneously introduced into a patient.

Figure 4A:
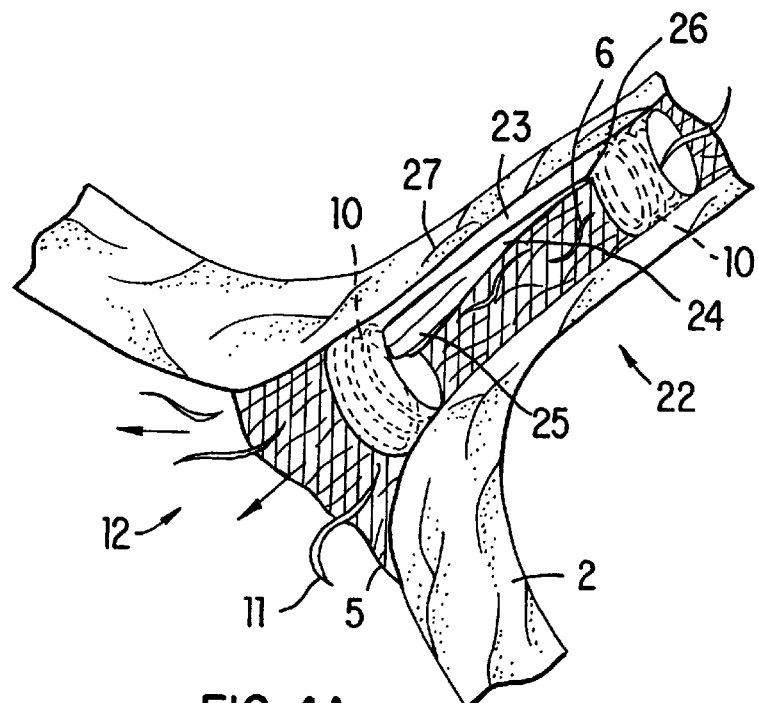
FIGS. 4A–B depict cut away views of a windsock-type prosthetic pulmonary vein valve, held in place by a proximal and distal anchoring stent, in open and closed positions, respectively.
Figure 4B:
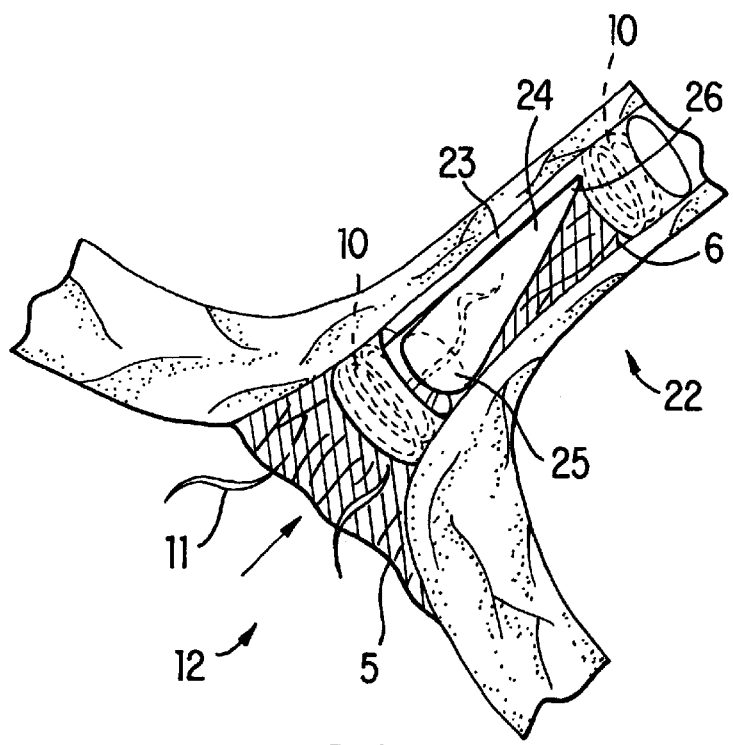
Figure 6:
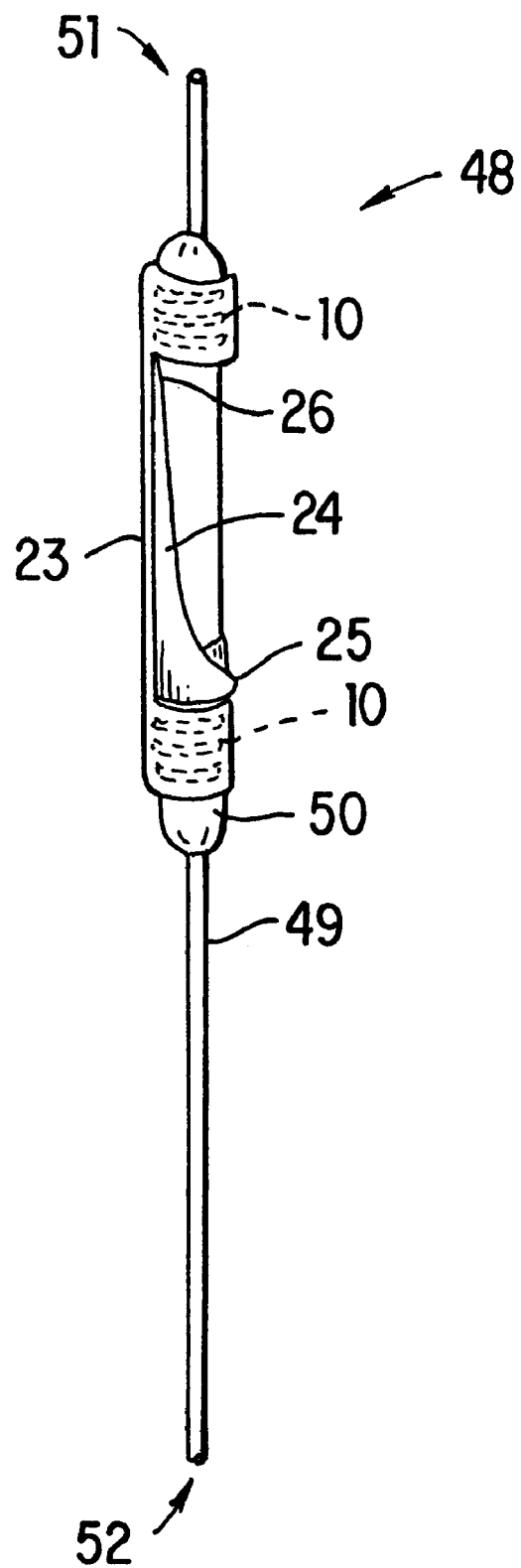
FIG. 6 depicts a device for surgically or percutaneously delivering a windsock-type prosthetic pulmonary vein valve.

FIGS. 4A and 4B are cut away views of a windsock type prosthetic pulmonary valve device (22), held in place in a pulmonary vein (6) by anchoring stents (10). The anchoring stents (10) are joined by a rigid spine (23), to which is attached a conically shaped (windsock-like) structure (24) fabricated of a flexible material. The device is positioned so that the wider end (25) of the cone-like structure (24) is closer to the left atrium than its narrower end (26). FIG. 4A illustrates that when the pressure (arrow) in the pulmonary vein exceeds the pressure in the left atrium (12), blood (11) flows past the conical structure (25), collapsing it against the wall of the vein (27) and the rigid spine (23), to which the conical structure is attached. Blood then flows into the left atrium. In contrast, as shown in FIG. 4B, when the pressure (arrow) in the left atrium is greater than that in the pulmonary vein, blood (11) flows into the conical structure (24), forcing its wider end (25) open, and the "inflated" conelike structure creates an obstruction to blood flow and/or pressure transmission from the left atrium into the pulmonary vein. Such windsock-type devices may be introduced by open surgical or percutaneous techniques; a method for percutaneous insertion is discussed below and a device for percutaneous insertion is illustrated in FIG. 6.

Prosthetic Pulmonary Vein Valve Delivery Systems

A pulmonary vein prosthetic valve delivery system is a means for delivery of the pulmonary vein prosthetic valve into a pulmonary vein, for positioning the pulmonary vein prosthetic valve in the desired implantation site, and for maintaining the desired position of the pulmonary vein prosthetic valve during its expansion (where applicable) to fit within the walls of the target pulmonary vein. Expansion of the prosthetic valve refers to changing the diameter of the prosthetic valve apparatus (or a subcomponent thereof) from an unexpanded configuration of smaller circumference and area to a final deployed configuration of larger circumference and area. Such change in the configuration of the prosthetic valve can be effected by means integral to the prosthetic valve itself (as with self-expanding prosthetic valves) or ancillary to it (non-self-expanding prosthetic valves). It should be noted that for the purposes of this disclosure, any partially or incompletely self-expanding prosthetic valve would be viewed as a non-self-expanding prosthetic valve. It should be further noted that the term balloon used hereafter is meant to apply to all ancillary means of expansion of non-self-expanding prosthetic valves. Anchoring of the expanded prosthetic valve refers to permanent or temporary retention of the expanded prosthetic valve in its intended location by means intrinsic to the prosthetic valve structure or a subcomponent thereof; for example, the diaphragm-type valves shown in FIGS. 1C and 1D are retained in position by an anchoring stent; in such and similar instances, the anchoring stent is considered a subcomponent of a prosthetic valve apparatus.

The delivery system must reliably disengage from the implanted pulmonary vein prosthetic valve, and be able to be removed from the pulmonary vein and out of the body of the valve recipient in a straightforward and reliable manner. A percutaneous prosthetic valve delivery system for a self-expanding valve additionally typically allows release of the self-expanding prosthetic valve after the self-expanding prosthetic valve is positioned in the desired location in its target. The following patents disclose examples of such systems: U.S. Pat. No. 5,332,402 by Teitelbaum; U.S. Pat. No. 5,397,351 by Pavenik et al.; U.S. Pat. No. 5,607,465 by Camilli; and U.S. Pat. No. 5,855,601 by Bessler et al.

In alternate embodiments, apercutaneous prosthetic valve delivery system for a non-self-expanding prosthetic valve may additionally provide for bringing the means for valve expansion, typically a balloon, to the valve positioned in the desired location. The following patents disclose examples of such systems: U.S. Pat. No. 5,163,953 by Vince, and U.S. Pat. No. 5,411,552 by Andersen et al. In a preferred non-limiting embodiment, the valve may be introduced by a shuttle catheter which utilizes an ancillary means of expansion, as described in U.S. Pat. No. 5,807,398 by Shaknovich.

The ostia of all four pulmonary veins are accessible percutaneously, using standard techniques, via a systemic vein, for example, a femoral or jugular vein, and then inferior or superior vena cava, respectively, to access first the right atrium, and then, via trans-atrial septal puncture, the left atrium. For example, the distal tip of a guiding catheter may be positioned against the fossa ovalis in the intra atrial septal wall and a Brochenbrough needle or trocar may be advanced distally through the guide catheter until it punctures the fossa ovalis after which the guiding catheter may replace the needle or trocar. Thus, the technique for percutaneous cannulation of the ostia of the pulmonary veins, and therefore for percutaneous implantation of prosthetic valves in the pulmonary veins, is directly analogous to existing and well-established methods and systems, for example, as currently used for ablation procedures in cardiac electrophysiology. The following patents disclose recent examples of such methods: U.S. Pat. No. 6,012,457 by Lesh and U.S. Pat. No. 6,064,902 by Haissaguerre et al.

Alternatively, and not by way of limitation, an ostium of a pulmonary vein may be accessed via the pulmonary vein itself, by a method referred to herein as the "pulmonary vein route" or "PV route". According to this method, a pulmonary vein is accessed and a prosthetic pulmonary vein valve is passed through the vein into a position at or near the ostium. Preferably, the prosthetic valve is passed using an appropriate device, which may be analogous to one of the devices described herein for percutaneous insertion. Unlike the percutaneous insertion devices, which are advanced in the direction from the left atrium toward or into a pulmonary vein, devices for insertion of valves via the PV route are advanced through a pulmonary vein toward the left atrium.

In particular non-limiting embodiments, the present invention provides for a tubular pulmonary vein prosthetic valve delivery catheter having a pulmonary vein prosthetic valve-carrying segment, upon which the pulmonary vein prosthetic valve can be mounted in a contracted or expanded condition and delivered into the desired location in a pulmonary vein. The pulmonary vein prosthetic valve may alternatively be (i) releasable and self-expandable to the desired degree; (ii) expandable to a desired degree by means intrinsic or ancillary to the pulmonary vein prosthetic valve-carrying segment of the pulmonary vein prosthetic valve delivery catheter; or (iii) expanded and of desired dimensions prior to surgical implantation.

Once in the desired position in a pulmonary vein or ostium, a pulmonary vein prosthetic valve may be retained in place by means intrinsic to the pulmonary vein prosthetic valve apparatus, such as, but not limited to, an anchoring stent, or by means extrinsic to it such as one or more staple(s), suture(s), and/or glue. Radiopaque and/or palpable markers may be used to identify the location of the pulmonary vein prosthetic valve on either the valve-carrying segment of the pulmonary vein prosthetic valve delivery catheter or after implantation.

A delivery system according to the invention may optionally comprise one or more retention sheath(s) which controllably prevent a self-expanding portion of the prosthetic pulmonary vein valve apparatus from expanding; such sheath(s) may be removed once the valve is in the desired position, permitting expansion and deployment of the valve. As one specific, non-limiting example, a delivery system may comprise proximal and distal retaining cuffs over the proximal and distal margins, respectively, of a prosthetic valve, which have attachments to the valve and the segments of the valve delivery catheter proximal and distal to the valve respectively. The retaining cuffs slide axially from the margins of the valve releasing the valve from the valve delivery catheter during self-expansion of the valve or during expansion of the valve and the valve-carrying segment of the valve delivery catheter by ancillary means.

A delivery system of the invention may in various embodiments comprise a balloon catheter, of which the expandable balloon segment is a pulmonary vein prosthetic valve-carrying segment, with a self-expanding or balloon-expandable pulmonary vein prosthetic valve attached to or mounted on it. Alternatively, the pulmonary vein prosthetic valve-carrying segment may be indirectly expandable (see, e.g., U.S. Pat. No. 5,807,398) with a balloon on a catheter that is separate and distinct from the pulmonary vein prosthetic valve delivery catheter, such catheter of the length that is greater than that of the pulmonary vein prosthetic valve delivery catheter, and which is reliably and repeatedly capable of advancing in unexpanded condition as well as collapsed condition through the entire length of the inner lumen of the pulmonary vein prosthetic valve delivery catheter and out of proximal end of the pulmonary vein prosthetic valve delivery catheter. Such an indirect expansion system is capable of complete and maximal expansion together of the pulmonary vein prosthetic valve and the expandable pulmonary vein prosthetic valve-carrying segment of the valve delivery catheter, and is capable of straightforward and reliable retraction from the valve deployment site alone or together with the pulmonary vein prosthetic valve delivery catheter.

Furthermore, pulmonary vein prosthetic valves and pulmonary vein prosthetic valve delivery systems of the invention may, in particular, non-limiting embodiments, be coated with or incorporate biological, chemical, pharmacological or radioactive substances, coatings or adhesives, including but not limited to antimicrobial, anticoagulant and/or antiproliferative substances. Examples of antiplatelet/anticoagulant substances that may be administered via or concurrently with or in conjunction with the prosthetic valves of the invention include warfarin, ticlopidine, low molecular weight and unfractionated heparin, hirudin, hirulog, and platelet glycoprotein receptor IIb/IIIa inhibitors.

The present invention provides for a prosthetic pulmonary vein valve delivery system comprising a tubular composite structure that permits in a straightforward, safe and reliable manner one or more of the following: i) prior to valve deployment, coaxial attachment of an unexpanded non-self-expanding valve; ii) attachment of such unexpanded valve to the interior of a segment of a self-expanding or non-self-expanding unexpanded anchoring stent expandable by the same means and to the same extent as necessary and sufficient for straightforward, safe and reliable expansion and anchoring of such valve; iii) advancement of the valve assembly into the desired location in the target pulmonary vein and maintenance of the desired position; iv) repeated, complete, proximal and distal coaxial advancement of the means of expansion of such valve and its anchoring element through the inner lumen of the structure; v) expansion of such valve to the desired extent by the intended use of the intended means of expansion for such valve; vi) disengagement of both the means of expansion of such valve and the structure from the expanded valve; and/or vii) retraction of both the means of expansion of such valve and the structure from the pulmonary vein, any guiding device and ultimately the patient.

In still other aspects, the present invention provides for methods and devices which, by way of example and not limitation, i) place and securely attach one or more prosthetic pulmonary vein valve(s) on the expandable valve-carrying segment of a valve delivery system; ii) maintain essentially without alteration the location of such valve on the expandable valve-carrying segment of the valve delivery system until expansion of such valve in the pulmonary vein by the operator; iii) protect such valve from damage or disruption during its passage to and within the pulmonary vein; iv) identify the location of such valve of the invention with markers clearly visible or palpable during the procedure; and v) sterilize, package, and label the assembly of such valve and the valve delivery system as is appropriate for its components and intended application(s).

The present invention also provides for various methods of inserting prosthetic pulmonary vein valves in subjects in need of such treatment.

In that regard, according to one embodiment, the present invention provides for a method for percutaneous deployment of a prosthetic pulmonary vein valve into one or more target pulmonary vein. This method may include some or all of the following steps: i) access to the right atrium is attained percutaneously with an appropriate size guiding catheter advanced into the right atrium, if necessary over a guide wire and an introducer, via a systemic, e.g. femoral, vein; ii) access to the left atrium by the same guiding catheter from the right atrium is attained, if necessary over a guide wire and an introducer, by means of transseptal puncture; iii) a guide wire is advanced under fluoroscopic guidance, if necessary with localizing injections of radiographic dye, through and out of the lumen of the said catheter now positioned in the left atrium, into the target pulmonary vein; iv) a prosthetic pulmonary vein valve delivery system of the invention, with such a valve securely attached and, in certain embodiments, ensheathed by a retention sheath, is coaxially mounted on the guide wire by passing the guide wire through the guide wire lumen of the delivery system; v) the delivery system of the invention is advanced coaxially over the guide wire, the distal portion of which is maintained in the target pulmonary vein, through and out of the lumen of the guiding catheter into the target pulmonary vein in the standard fashion, with the proximal end of the delivery system outside the patient at all times; vi) the distal end of the delivery system, comprising the prosthetic valve, is advanced into the desired location in the target pulmonary vein over the guide wire; and vii) the prosthetic pulmonary valve apparatus is manipulated so as to be deployed within or at the ostium; for example, where a retention sheath is used together with a self-expandible valve or anchoring stent, the retention sheath may be withdrawn, permitting expansion of the hitherto restrained element.

In the foregoing method, for embodiments wherein the valve is attached to the valve-carrying segment comprising a self-expanding anchoring stent, retraction of the retention sheath permits release and expansion of the valve-carrying segment, and consequent expansion of the valve and its anchoring in the target pulmonary vein. After the implantation of the valve, the delivery system is removed out of the patient. Where implantation of more than one prosthetic pulmonary valve is desired, the guide wire may then be repositioned in a second pulmonary vein, and the process may be repeated, until prosthetic valves are successfully implanted in all of the desired pulmonary veins.

Figure 5A:
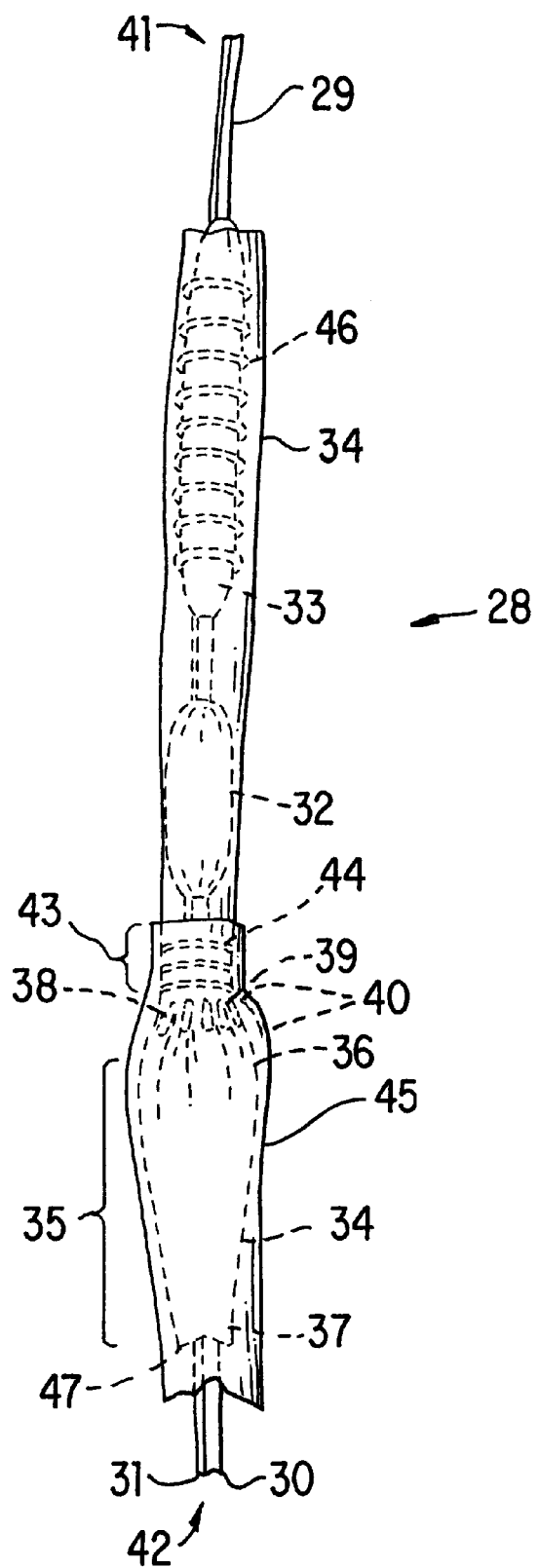
FIGS. 5A–E depict a device (A) and method (B–E; shown by cut away views) for surgically or percutaneously inserting a diaphragm-type prosthetic pulmonary vein valve.

In accordance with yet another aspect of this invention, this invention provides for methods for surgical deployment of one or more prosthetic pulmonary vein valve into a target pulmonary vein during an open-heart procedure. One non-limiting example of such a method includes the following steps: i) with the patient on heart lung bypass, access to the left atrium is attained using standard surgical techniques; ii) a prosthetic pulmonary vein valve delivery system of the invention (for example, as depicted in FIG. 5A), with such a valve securely attached and wherein the valve is covered by a protective sheath (see infra), is inserted into the target pulmonary vein through the ostium of the target pulmonary vein that is visualized directly by the implanting surgeon; iii) the distal end of the delivery system, comprising the prosthetic valve, is advanced into its desired location position in the target pulmonary vein; and iv) the protective sheath is withdrawn, exposing the valve-carrying segment of the delivery system. For the embodiment wherein the valve is attached to the valve-carrying segment comprising a self-expanding stent, retraction of the protective sheath permits release and expansion of the valve-carrying segment, and consequent expansion of the said valve and its anchoring in the target pulmonary vein. After the implantation of the valve, the said delivery system is removed out of the patient.

If surgical implantation of prosthetic valves in more than one pulmonary vein is desired, the ostium of a second pulmonary vein is then identified, and the process m ay be repeated until prosthetic valves are successfully implanted in as many of the pulmonary veins as is de sired. For the embodiment wherein the valve is attached to a valve-carrying segment comprising a non-self-expanding anchoring stent mounted on an appropriately sized balloon, expansion of the stent in the desired location in the target pulmonary vein may be achieved by inflating the balloon portion of the delivery system to the appropriate pressure.

Another method for implanting a prosthetic valve in a pulmonary vein comprises the following steps: i) with the patient on heart lung bypass, access to the left atrium is attained using standard surgical techniques; ii) the ostium of a pulmonary vein is identified; iii) a diaphragm-type or trapdoor-type prosthetic device with a mobile non-porous segment of the diameter greater than that of the ostium of the target pulmonary vein, is attached, for example by sutures, to the inner aspect of the left atrium in such a fashion that, when the pressure in the left atrium exceeds that in the pulmonary vein, this mobile segment is brought into opposition with the segment of the inner wall of the left atrium containing the ostium of the pulmonary vein, occluding the said ostium. When the pressure in the pulmonary vein exceeds that in the left atrium, the mobile segment of the valve is displaced into the left atrial cavity away from the inner aspect of the wall of the left atrium, allowing flow from the target pulmonary Vein into the left atrium. (see, for example, FIGS. 1C, 1D, 2C, 2D, 3A, 3B, 4A and 4B). The ostium of a second pulmonary vein may then be identified, and the process may be repeated, until said prosthetic valves are successfully implanted in the desired number of pulmonary veins.

According to still further embodiments, this invention provides for a method for deployment of a prosthetic pulmonary venous valve into one or more target pulmonary vein(s) via the PV route. This method may include the following steps: i) the pulmonary vein is localized either visually or by laparoscopic means; ii) an entry point for a prosthetic device is made in the pulmonary vein; for example, but not by way of limitation, a purse-string suture is created in the vein and a nick is created in the middle of the area enclosed by the suture (such that blood flow out of the nick may be controlled by drawing the suture); iii) a prosthetic device as part of a delivery system is inserted (e.g. over a guide wire) through the nick into the pulmonary vein and then advanced into the left atrium; and then iv) the prosthetic device is moved into position and deployed at the ostium of the pulmonary vein. The position of the device may be monitored, for example, fluoroscopically (where the tip of the device is radioopaque). Alternatively, the device may comprise a reverse-break segment which, in expanded form, can be wedged at the ostium. In particular embodiments, the delivery system may comprise a prosthetic device having a fixing mechanism, such as a stent or suture/staple element, at the leading edge (advanced into the left atrium) with the valve trailing behind.

In accordance with yet another aspect of this invention, this invention includes a method for remote monitoring of flow and pressure across the implanted prosthetic pulmonic valve, and blood temperature and oxygen saturation wherein available technology for measuring these parameters is comprised in a pulmonary vein prosthetic valve.

Particular, non-limiting embodiments of prosthetic valve percutaneous delivery systems and methods of the invention are depicted, using cutaway views, in FIGS. 5A–E and FIG. 6.

FIGS. 5A–E illustrate a device and method for surgically or percutaneously introducing a diaphragm—type pulmonary vein prosthetic valve in a patient. FIG. 5A illustrates an apparatus (28) for delivering such a valve device having a distal end (41) and a proximal end (42). As used herein, the relative terms "distal" and "proximal" refer to the direction defined by the positions of the left atrium and a pulmonary vein—elements closer to the pulmonary vein are considered distal, and those closer to the left atrium, or, for percutaneous embodiments, the site of insertion into the body of the patient, are proximal. The apparatus comprises a catheter (29), which comprises separately controlled air channels (30, 31) for independent expansion of a proximal brake-segment balloon (32) and a distal stent-deployment balloon (33). A flexible, stretchable material having an approximately tubular conformation extends over both balloons (34), a portion of which is destined to become the occluder portion (35) of the valve device and which has a larger diameter distally (36) than proximally (37), such that the distal region is somewhat collapsed around the catheter. In particular embodiments, portion (35) may comprise an essentially circular piece of flexible, stretchable material, with an opening (47) at its center through which catheter (29) may pass. Distal to occluder portion (35) is a region (40) comprising fenestrations (38) and bridging arms (39). Distal to region (40) is a portion (43) of tubular material (34) which overlies self-expanding stent (44), which is restrained from expanding by retractable protective sheath (45). A non-selfexpanding stent (46) is mounted over balloon (33).

Figure 5B:
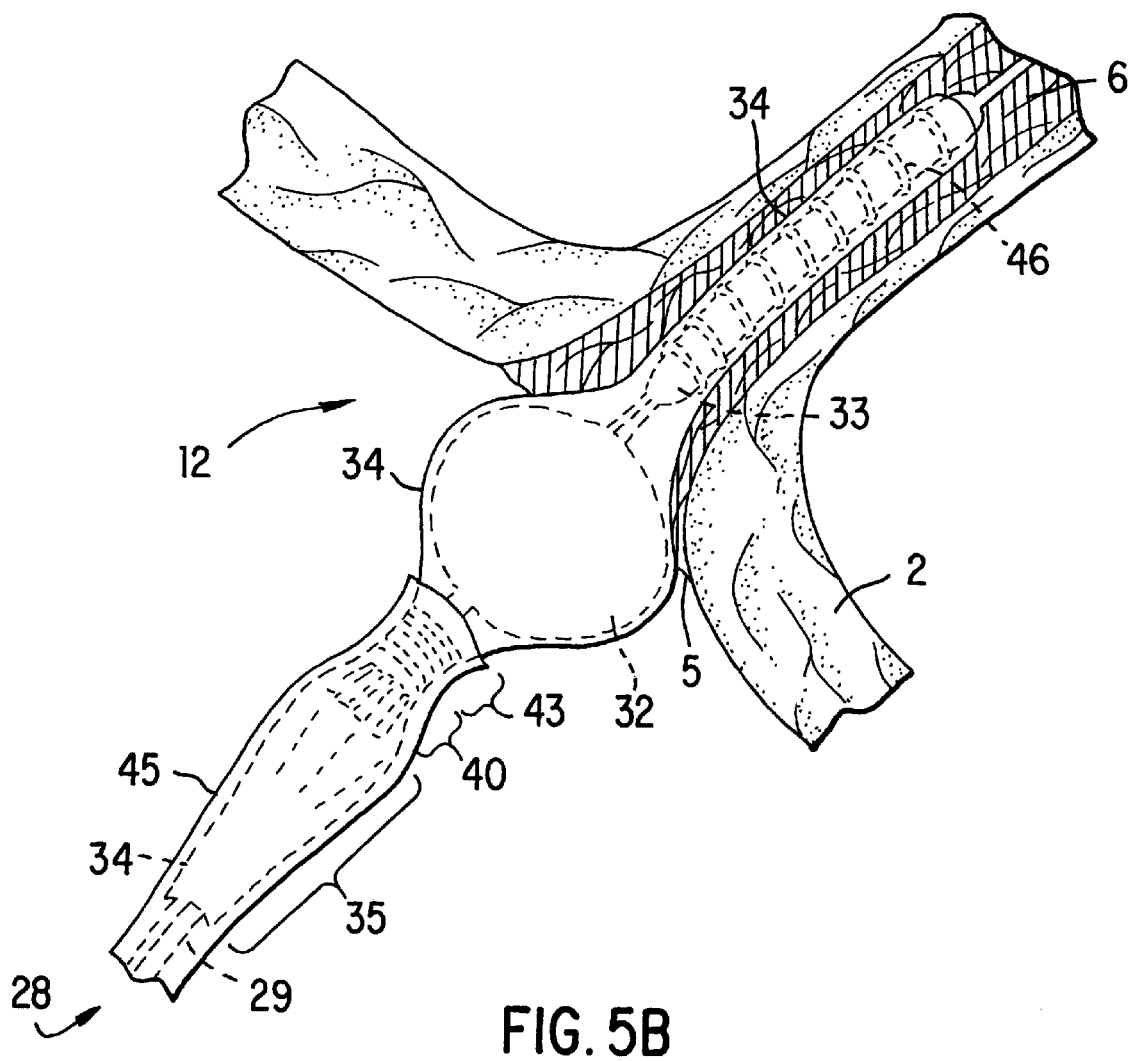

FIGS. 5B–E depict a method of using the apparatus (28) shown in FIG. 5A. As shown in FIG. 5B, the distal end of catheter (29) may be introduced into the left atrium (12) over a guide wire (not shown) and through a guiding catheter (not shown), according to techniques as discussed above and well known in the art. Under fluoroscopic guidance, the catheter (29) may be introduced into pulmonary vein (6). The location of the ostium (5) of the pulmonary vein (6) may be ascertained by inflating brake-segment balloon (32) and then advancing apparatus (28) distally until the inflated balloon wedges in the ostium (5). Balloon (32), and its structural relationship to balloon (33) and its overlying stent (46), not only localizes the pulmonary vein ostium(5), but also puts anchoring stent (46) in the desired position in the pulmonary vein (6), and stabilizes this position (as set forth with regard to the ostial delivery system in U.S. Pat. No. 5,749,890).

Figure 5C:
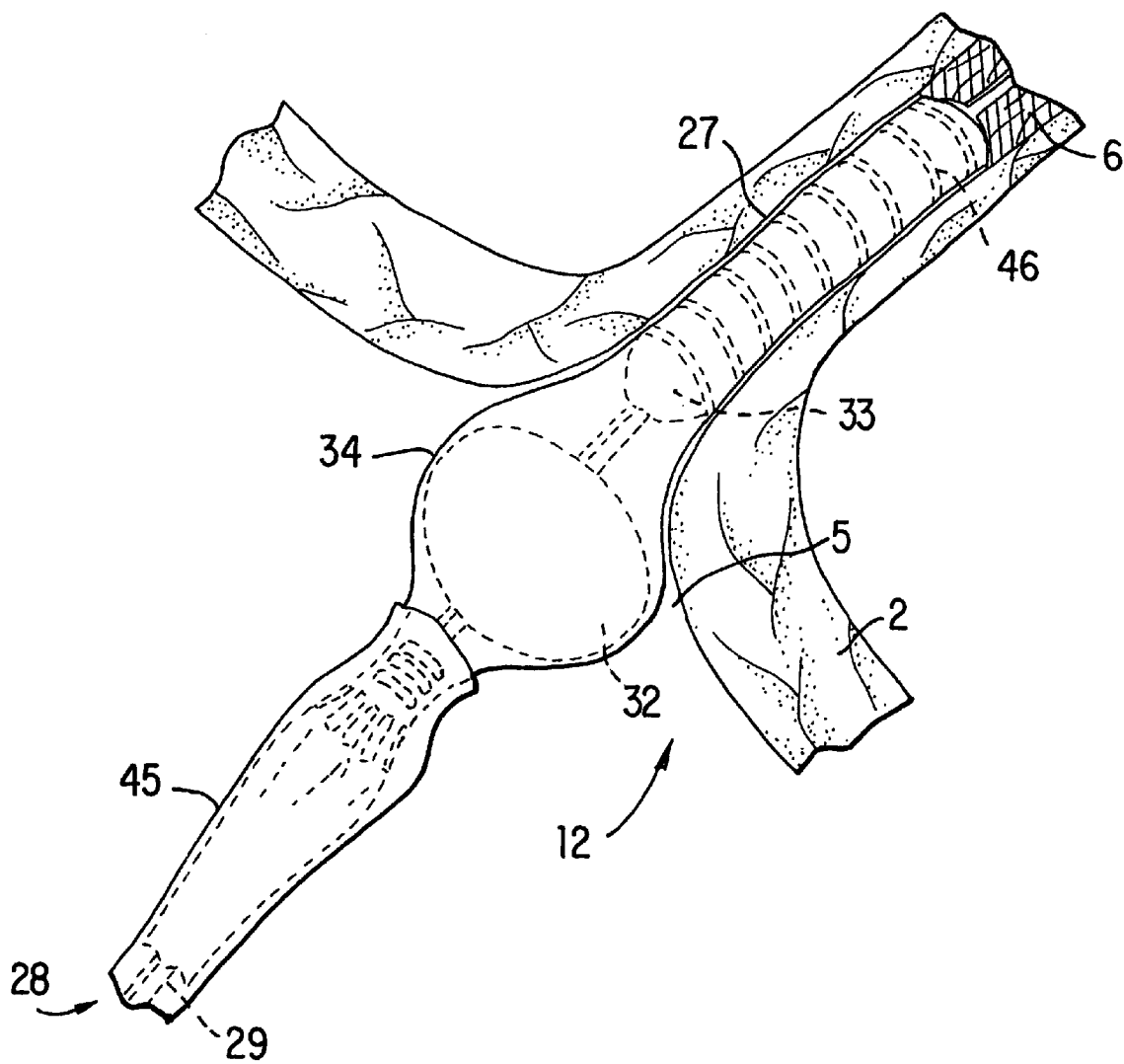

Next, as shown in FIG. 5C, with the brake-segment balloon (32) inflated and stabilizing the positioning of apparatus (28), balloon (33) may be inflated, thereby expanding and deploying anchoring stent (46), which will then retain tubular material (34) in apposition to the pulmonary vein wall (27).

Figure 5D:
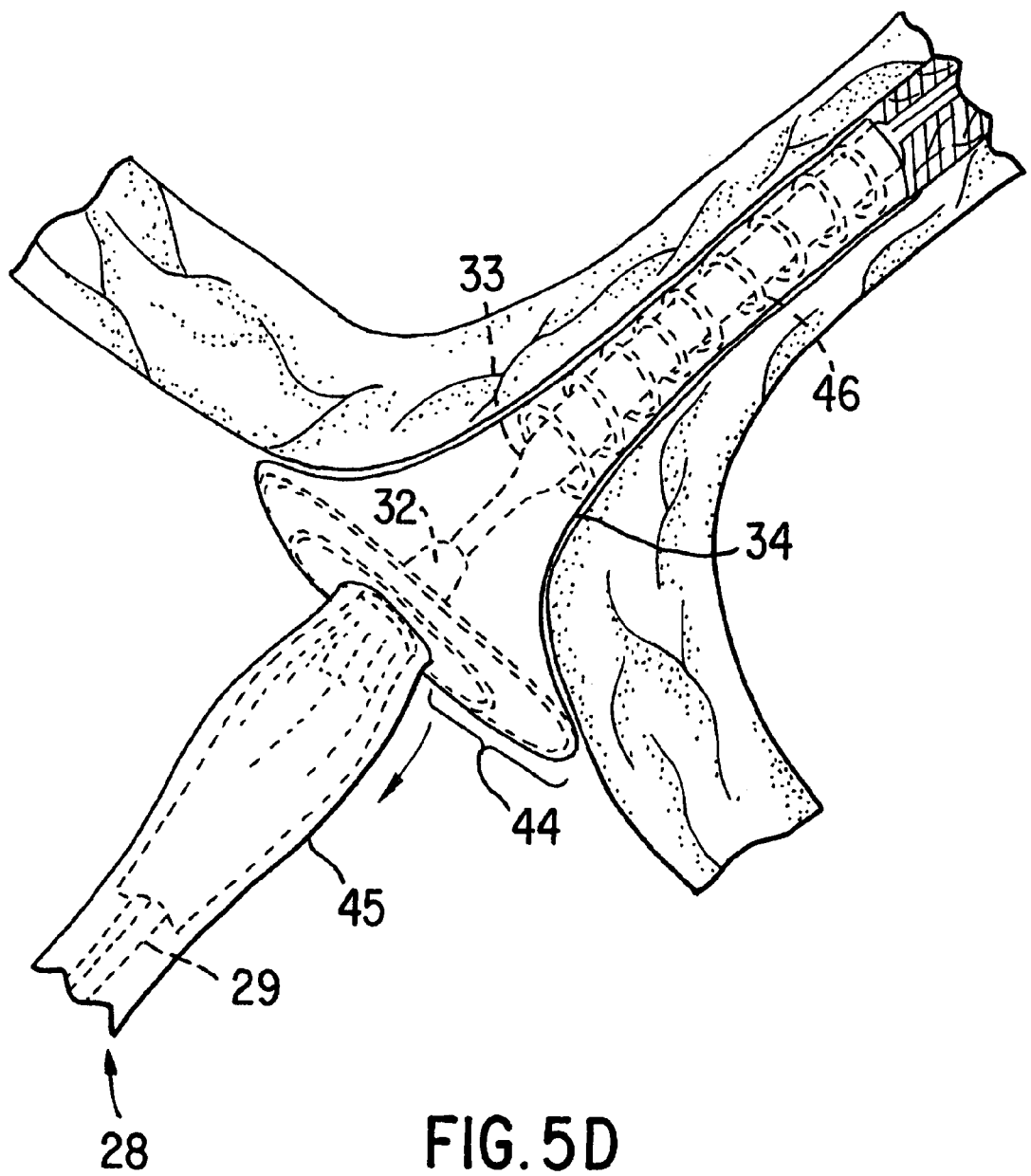

Subsequent to deployment of anchoring stent (46), as shown in FIG. 5D, balloons (32) and (33) may be deflated, and the protective sheath (45) may be retracted, permitting expansion of self-expanding stent (44).

Figure 5E:
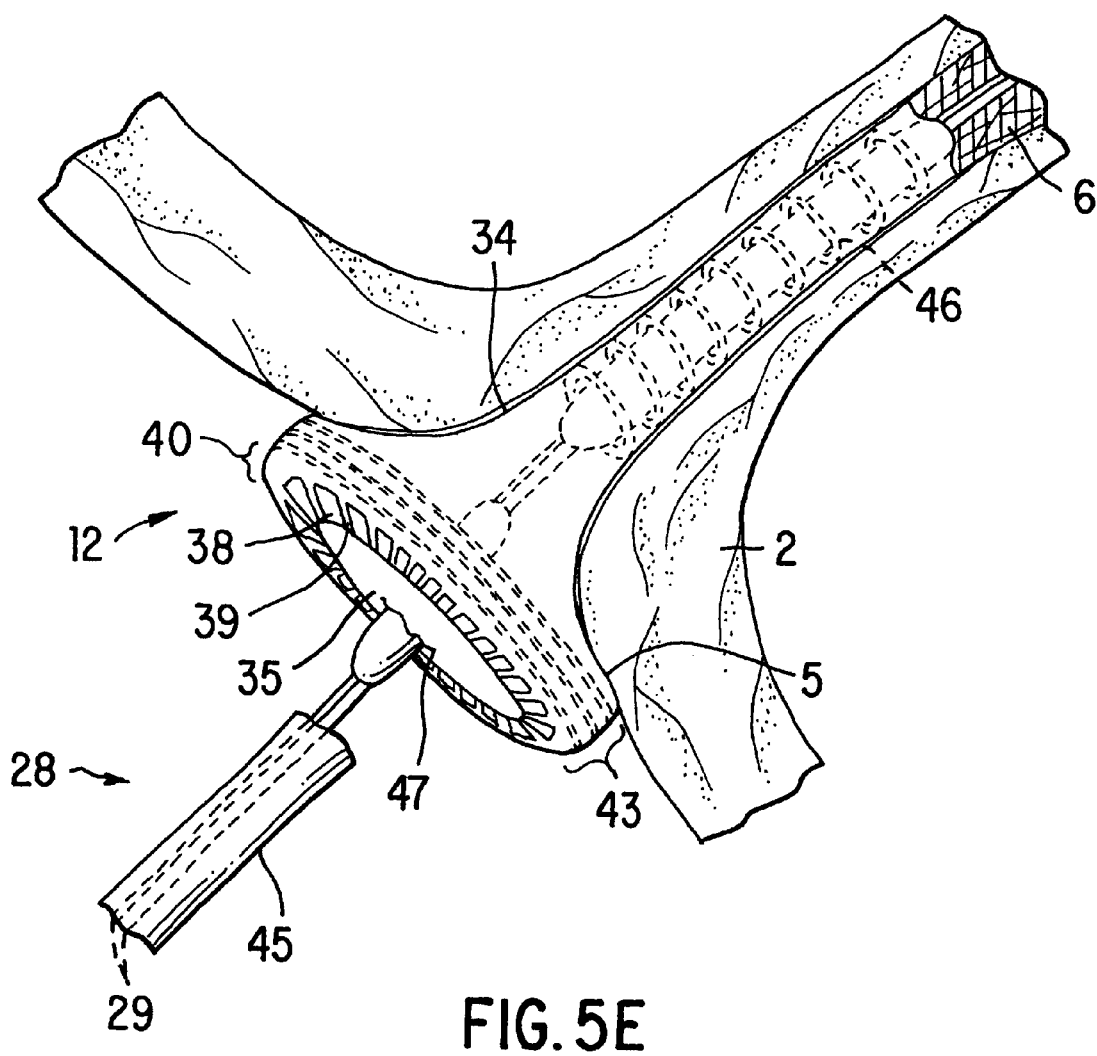

FIG. 5E shows that when the stent (44) is expanded, region (35) forms the occluder portion of the valve device, surrounded by region (40), with its fenestrations (38) and bridging arms (39). Self-expanding stent (44), contained in the structure (34), has a diameter which is greater than the diameter of the pulmonary vein, such that it overlies or lies in the ostium (5). Catheter (29) and integrated structures may then be withdrawn from the deployed valve device, and then out of the patient, through opening (47). Once the catheter is removed, opening (47) may permit some blood flow during various points of the cardiac cycle, or may, optionally, be configured so that blood flow in at least one direction is obstructed; for example, the opening may be configured as a slit with overlapping edges, so that with increased pressure one edge is pressed against the other edge, thereby creating a seal.

FIG. 6 depicts an apparatus (48) for surgical or percutaneous introduction of a windsock-type pulmonary vein prosthetic valve. The apparatus, which has distal (51) and proximal (52) ends, comprises a catheter (49) carrying a balloon (50), upon which the device is mounted. As set forth above and as illustrated in FIGS. 4A and 4B, the valve device includes anchoring stents (10), joined by a rigid spine (23), to which is attached a conically shaped (windsock-like) structure (24) fabricated of a flexible material. The wider end (25) of the cone-like structure (24) is located closer to the proximal end of the balloon, and is wrapped around the balloon (50). The stents may be non-self expanding, and therefore deployable by inflation of the balloon, or may be self-expanding, in which case the valve-device carrying portion of the apparatus may be completely or partially covered by one or more retractable sheath (not shown). The valve device may be surgically or percutaneously introduced into a patient by inserting the distal end of apparatus (48) into the left atrium, placing the valve device, compressed on the balloon, into the pulmonary vein, such that both anchoring stents (10) are within the vein, and then inflating the balloon (50), thereby deploying the valve device.

Analogous devices may be used to deliver prosthetic pulmonary vein valves via the PV route. FIGS. 7A–G illustrate a device and method for introducing a diaphragm—type pulmonary vein prosthetic valve in a patient via the PV route.

Figure 7A:
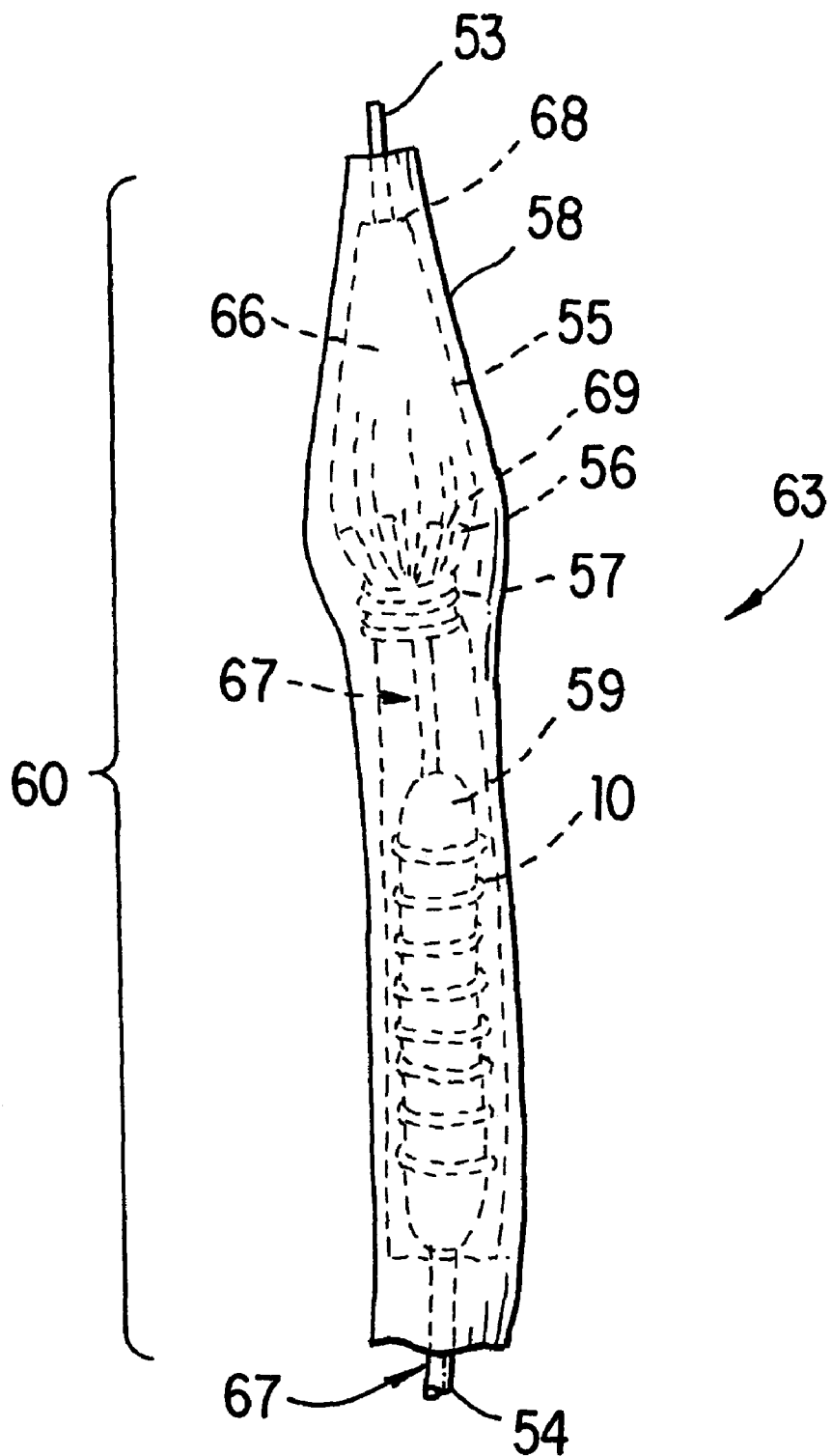
FIGS. 7A–G depict a device (A) and method (B–G; shown by cut away views) for inserting a diaphragm-type prosthetic pulmonary vein valve via the pulmonary vein ("PV") route.

FIG. 7A illustrates an apparatus (63) for delivering such a valve device having a first end (53) which serves as the leading tip of the device as it is passed through the pulmonary vein and into the left atrium, and a second end (54) which extends from the valve deploying portion of the device (60) to a position outside of the pulmonary vein, where it is under the control of the surgeon. The apparatus comprises a catheter (67) and, from first end (53) toward second end (54), a self-expanding stent (57) and a stent-deployment balloon (59) onto which is mounted an expandable anchoring stent (10). A flexible, stretchable material having an approximately tubular conformation (55) extends from the first end of the device (53) over the self-expanding stent (57) and the stent-carrying balloon (59). A portion of this stretchable tubular material (55), which is destined to become the occluder portion (66) of the valve device, has a larger diameter in the region of the self-expanding stent (57) than at the tip of the device (53), such that, in the region of the self-expanding stent, the material is somewhat collapsed around the catheter. In particular embodiments, portion (66) may comprise an essentially circular piece of flexible, stretchable material, with an opening (68) at its center through which catheter (67) may pass. Between the portion of the stretchable material destined to become the occluder portion 66 and the portion overlying the self-expanding stent (57) is a region containing fenestrations (56) separated by bridging arms (69) which are approximately parallel to the central axis and to the catheter (67). The foregoing structures are enclosed, prior to valve placement, by a tubular retention sheath (58), which restrains the self-expanding stent (57) from expanding.

Figure 7B:
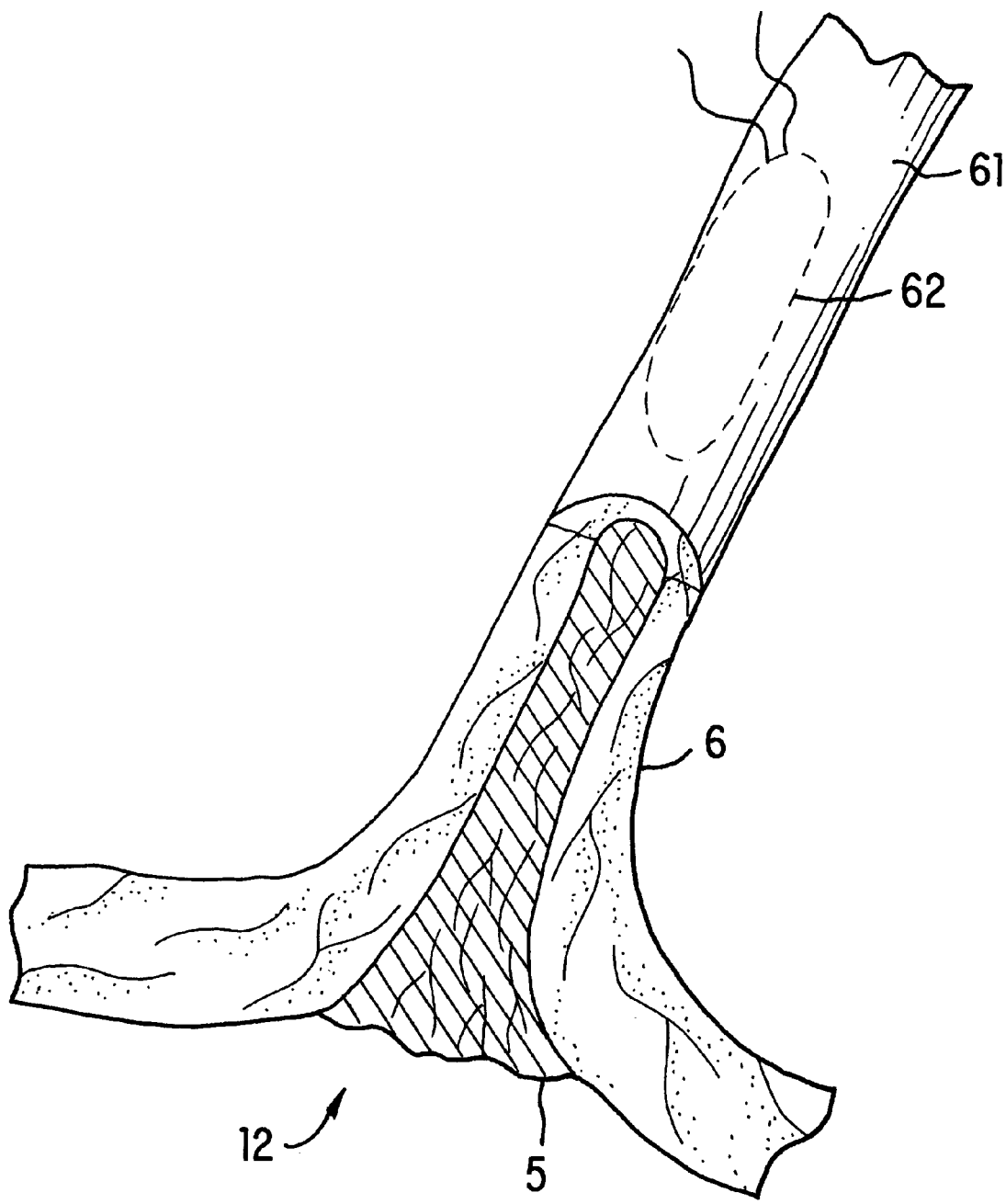
Figure 7C:
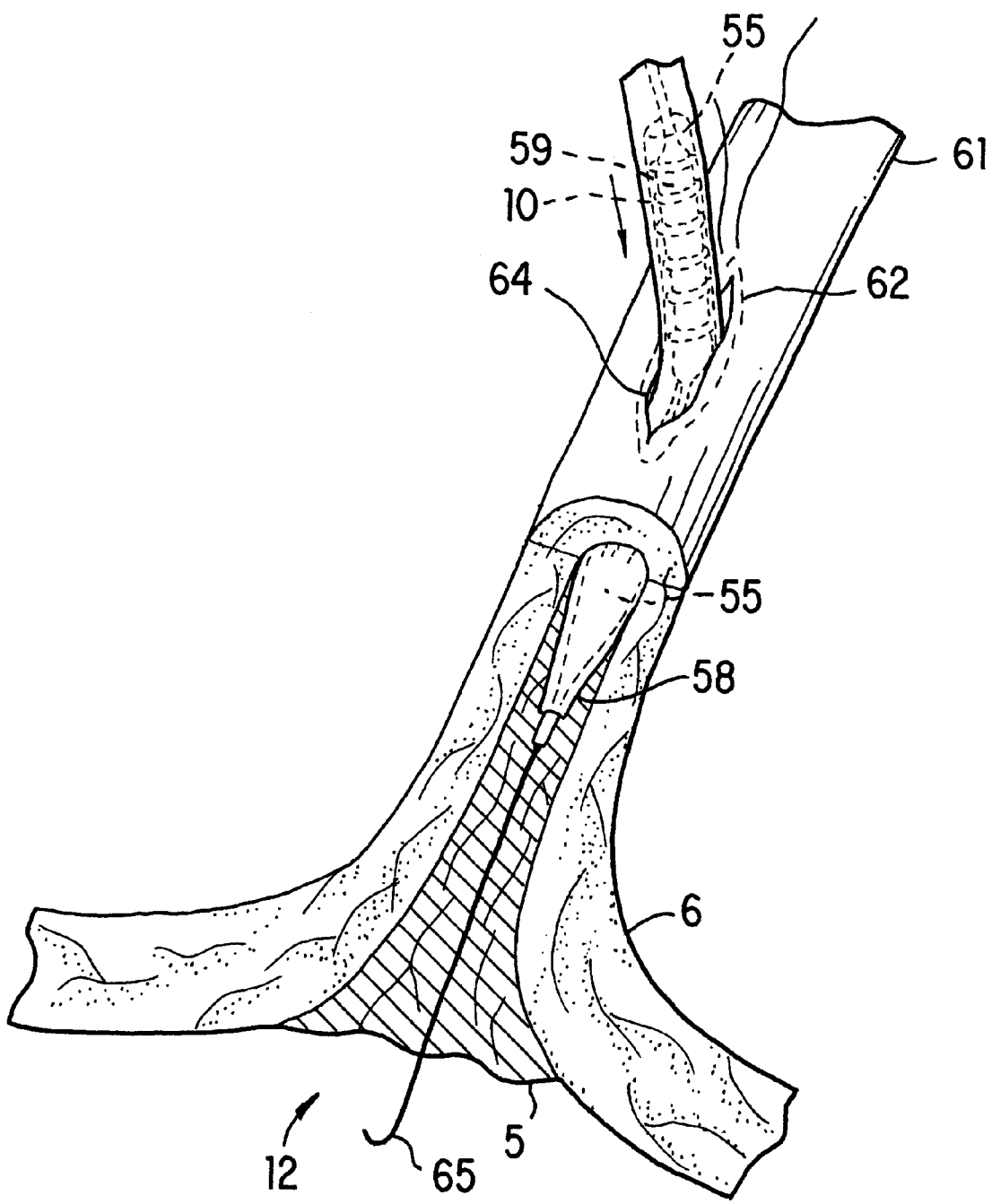
Figure 7D:
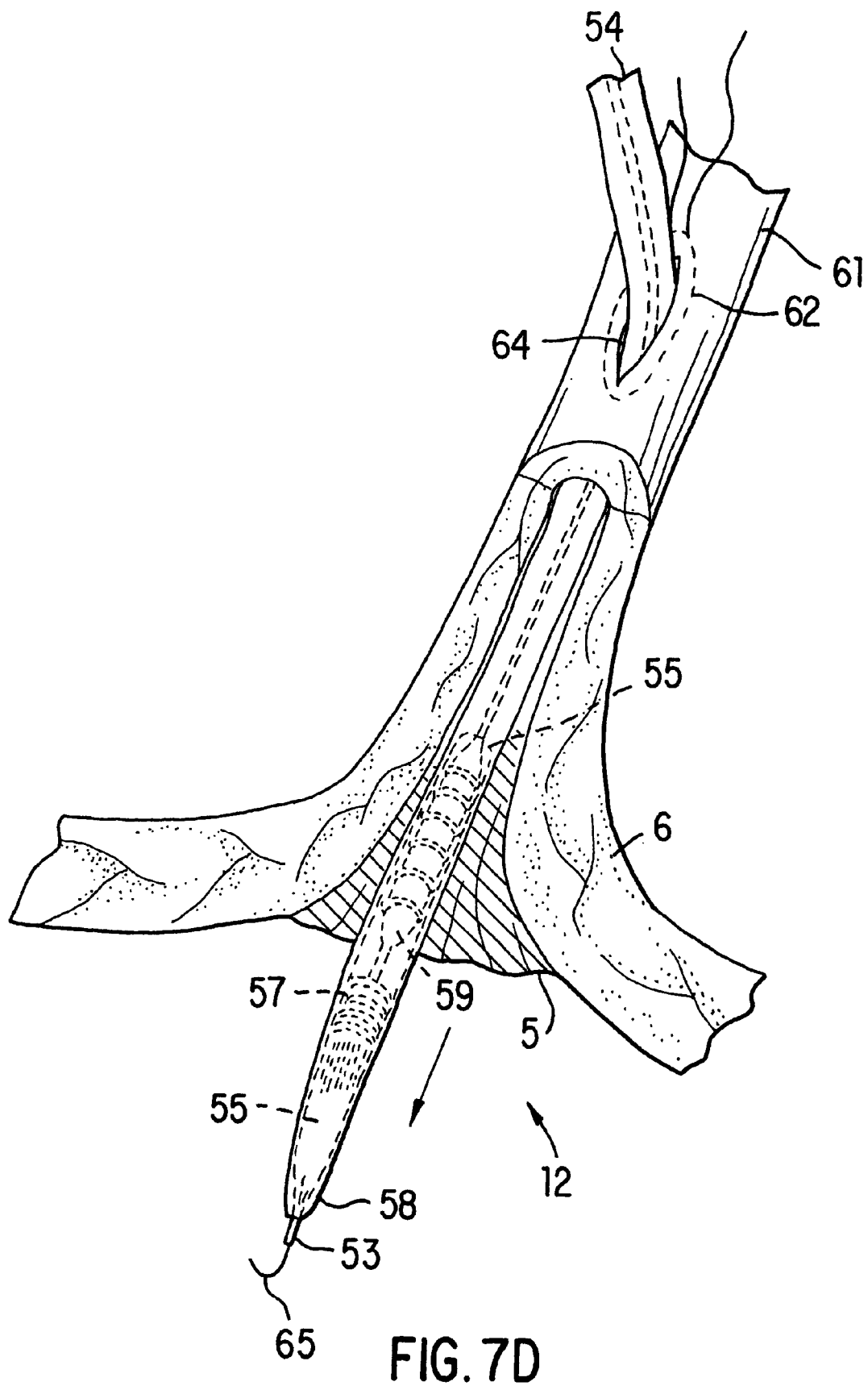
Figure 7E:
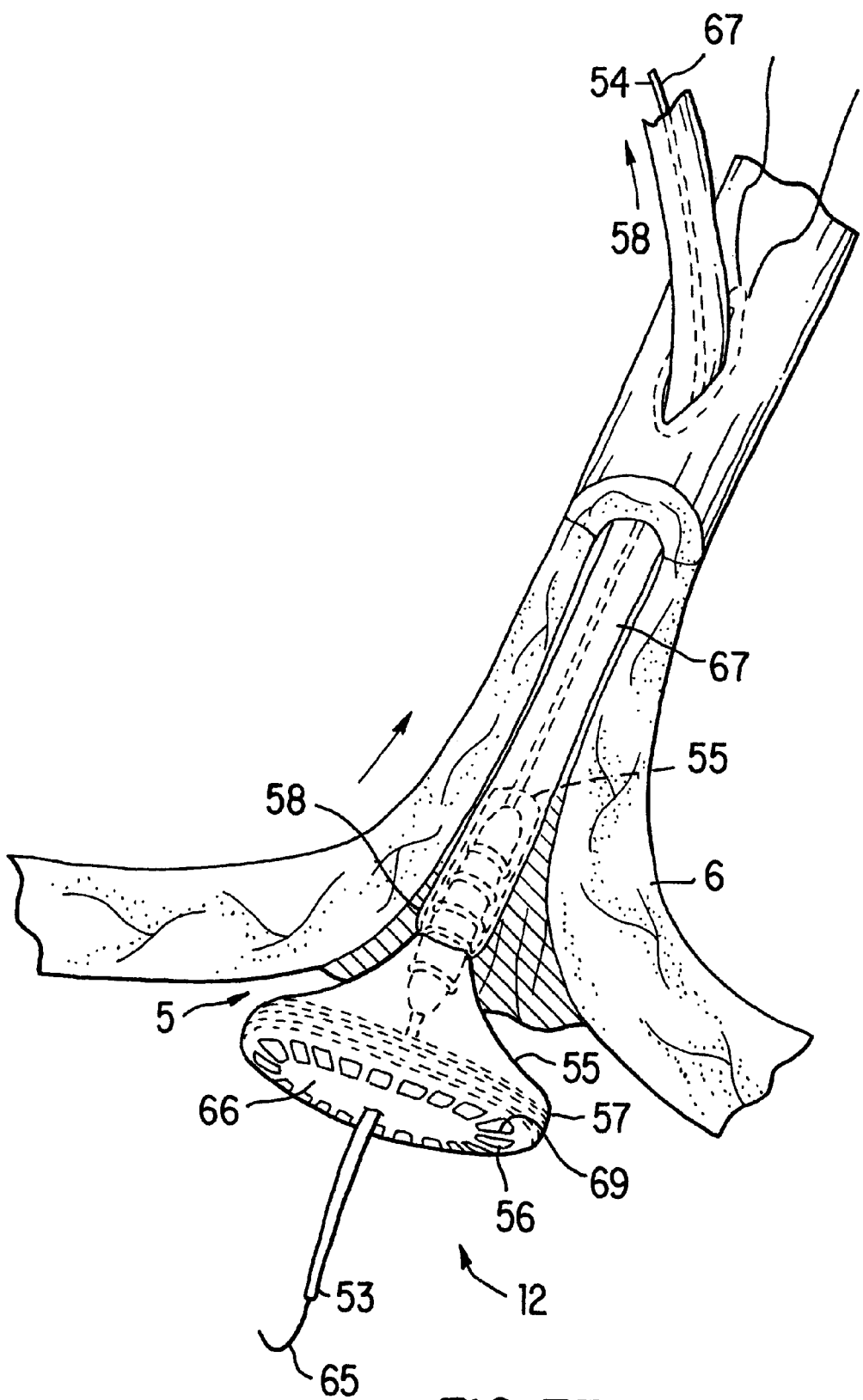
Figure 7F:
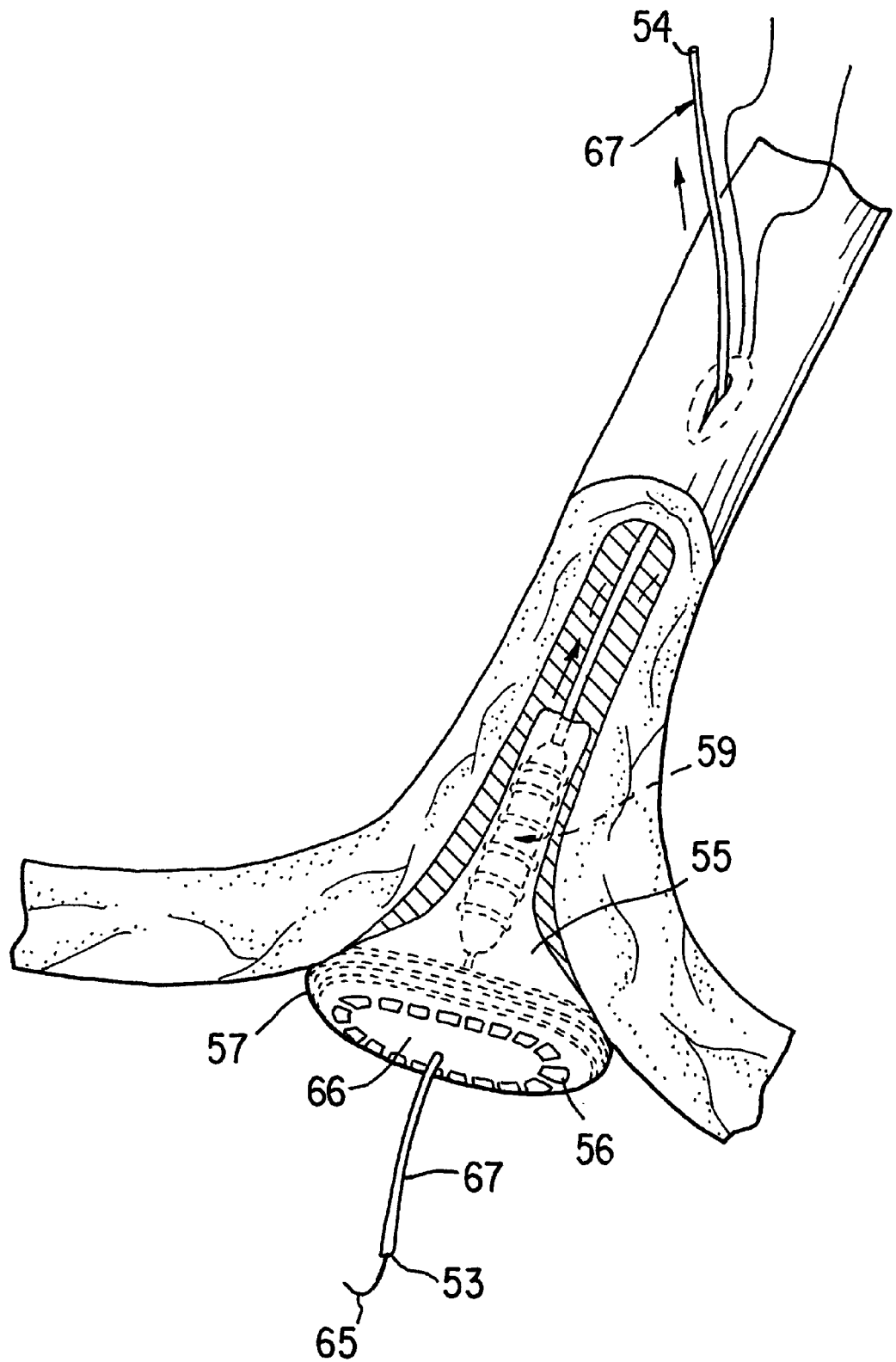
Figure 7G:
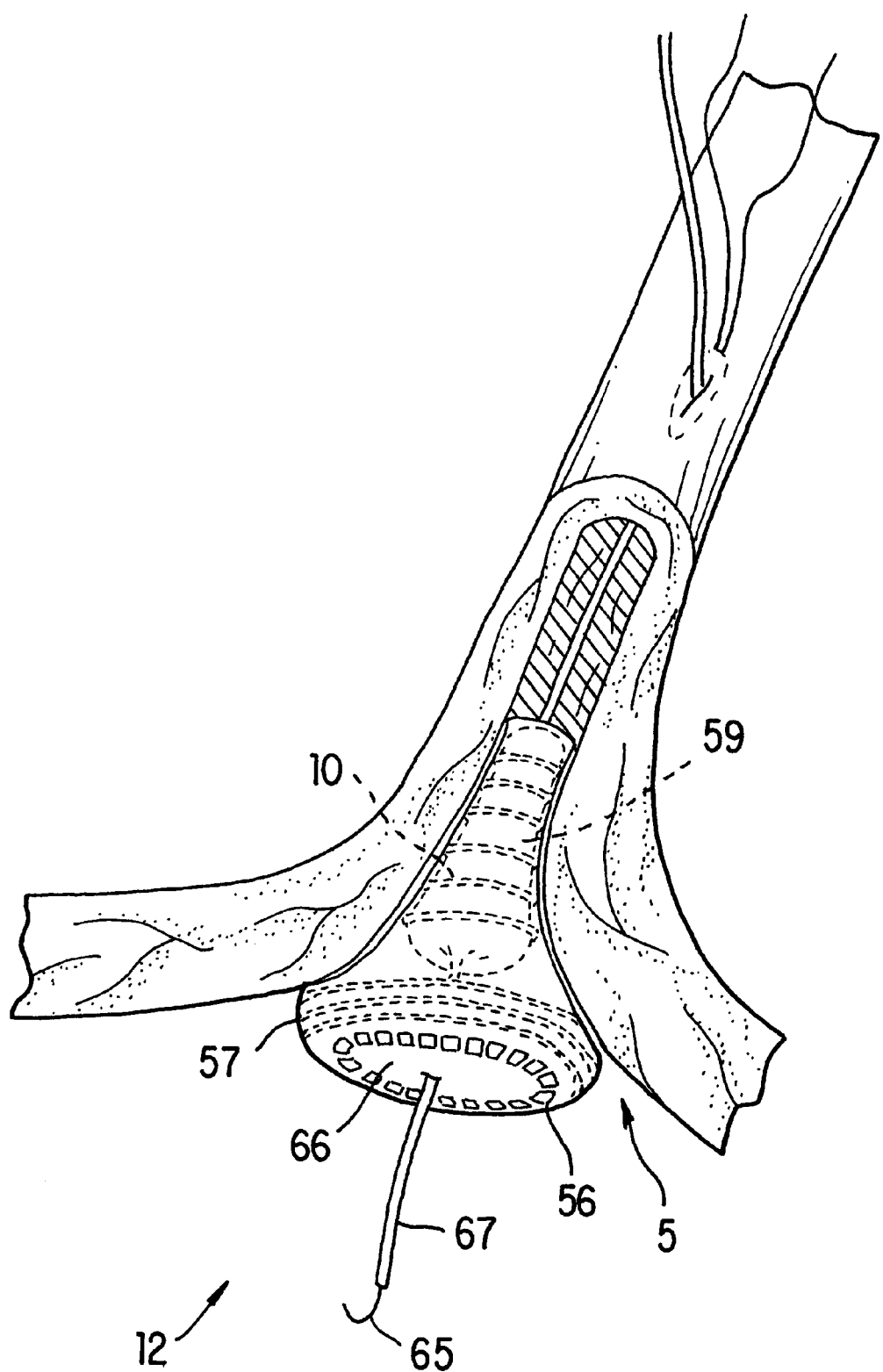

FIGS. 7B–G depict, using cut-away views, a method of using the apparatus (63) shown in FIG. 7A. As shown in FIG. 7B, which depicts an intact portion of a pulmonary vein (6) having an outer surface (61) showing a purse-string suture (62). Also shown in FIG. 7B are the ostium (5) of the pulmonary vein (6) and the left atrium (12). As shown in FIG. 7C, a deployment device according to FIG. 7A may be introduced into a nick (64) made within the purse-string suture (62), optionally over a guide wire (65). An arrow shows the direction in which the device is being inserted into the vein. The device may be advanced such that the first end (53) lies within the left atrium (12), as shown in FIG. 7D. Then, as depicted in FIG. 7E, the retention sheath (58) may be pulled back (in the direction of the arrow), allowing self-expanding stent (57) to expand and stretch the stretchable tubular material (55) so as to form the occluder portion (66) having fenestrations (56) separated by bridging arms (69). Once the diaphragm-type valve has been created by expansion of stent (57), the device may be pulled back, as shown in FIG. 7F (see direction shown by arrows), such that it lodges over the ostium and essentially acts as its own "brake segment". Then, as shown in FIG. 7G, the anchoring stent (10) may be deployed by expanding balloon (59). Afterwards, the balloon may be deflated and the catheter (67) and guide wire (65) may be withdrawn from the patient.

It should be noted that other designs of delivery device, such as that shown in FIG. 6, may be adapted for valve deployment via the PV route. For example, the device shown in FIG. 6 may be introduced into a nick in a pulmonary vein with end (51) as the leading edge. Its position in the pulmonary vein may then be ascertained manually or, for example, fluoroscopically where the device comprises a radioopaque marker. The device may be deployed by expanding the balloon such that the anchoring stents 10 are fixed in position in the vessel at the appropriate location.

In accordance with yet another aspect, this invention includes a method for treatment of target pulmonary vein obstruction due to malfunction of certain types of prosthetic pulmonary vein valves. For example, a windsock-type prosthetic pulmonary vein valve implanted into a pulmonary vein may cause partial or complete obstruction of the target pulmonary vein due to formation of thrombus in the sock portion of the valve. The thrombus may interfere, completely or to a significant degree, with compression and displacement of the expanded sock portion of the valve when pressure in the target pulmonary vein proximal (i.e. further away from the left atrium) to the prosthetic valve exceeds pressure in the target pulmonary vein distal (i.e. closer to the left atrium) to the prosthetic valve.

One non-limiting example of a method for treatment of partial or complete obstruction of the target pulmonary vein by such a malfunctioning wind-sock valve includes the following steps: i) access to the right atrium is attained percutaneously with an appropriate size guiding catheter advanced into the right atrium, if necessary over a guide wire and an introducer, via a systemic, e.g. femoral, vein; ii) access to the left atrium by the same guiding catheter from the right atrium is attained, if necessary over a guide wire and an introducer, by means of transseptal puncture; iii) a guide wire is advanced under fluoroscopic guidance, if necessary with localizing injections of radiographic dye, through and out of the lumen of the catheter now positioned in the left atrium, into the segment of the target pulmonary vein between the left atrium and prosthetic valve; iv) the guide wire is then manipulated past the malfunctioning thrombosed wind-sock prosthetic pulmonary vein valve, if necessary with localizing injections of radiographic dye; v) a new delivery system with a new prosthetic valve is advanced coaxially over the said guide wire, the distal portion of which is maintained in the target pulmonary vein, through and out of the lumen of the guiding catheter into the target pulmonary vein in the standard fashion, with the proximal end of the delivery system outside the patient at all times; vi) the distal end of the delivery system, comprising the valve, is advanced into the desired location overlapping the thrombosed previously implanted valve in the target pulmonary vein over the guide wire; vii) the new prosthetic valve is deployed as described above, compressing the malfunctioning first valve against the wall of the target pulmonary vein and restoring unidirectional flow out of the target pulmonary vein into the left atrium. As an alternative to inserting a new prosthetic valve, a stent may be implanted into the malfunctioning first valve, relieving the obstruction without creating a partitioning between the target pulmonary vein and the left atrium.

Various references are cited herein, the contents of which are hereby incorporated by reference in their entireties.

I claim:

1. A method of lowering mean pulmonary venous pressure in a subject, comprising creating an effective unidirectional partitioning between the left atrium and a pulmonary vein of the subject.

2. The method of claim 1, where unidirectional partitioning is achieved by implanting a prosthetic valve in a location selected from the group consisting of a pulmonary vein, an ostium of a pulmonary vein, and a left atrium.

3. The method of claim 1, where partitioning is achieved between the left atrium and more than one pulmonary vein.

4. The method of claim 3, where partitioning is achieved between the more than one pulmonary vein and the left atrium by implanting, as to each pulmonary vein subject to partitioning, a prosthetic valve in a location selected from the group consisting of the pulmonary vein, the ostium of the pulmonary vein, and the left atrium.

5. The method of claim 1 which is used for the treatment of congestive heart failure in the subject.

6. The method of claim 2 which is used for the treatment of congestive heart failure in the subject.

7. The method of claim 2, where the prosthetic valve is a diaphragm-type pulmonary vein prosthetic valve device.

8. The method of claim 2, where the prosthetic valve is a trapdoor-type pulmonary vein prosthetic valve device.

9. The method of claim 2, where the prosthetic valve is a stocking-type pulmonary vein prosthetic valve device.

10. The method of claim 2, where the prosthetic valve is a windsock-type pulmonary vein prosthetic valve device.

11. The method of claim 2, where the prosthetic valve is implanted by percutaneously accessing the pulmonary vein ostium.

12. The method of claim 2, where the prosthetic valve is implanted by an open-heart surgical procedure.

13. The method of claim 2, where the prosthetic valve is implanted by a method comprising: (i) surgically accessing the pulmonary vein; (ii) introducing the prosthetic valve first into the pulmonary vein and then advancing the prosthetic valve to the ostium; and (iii) deploying the prosthetic valve in the desired location.

* * * * *